US 9,221,077 B2

(12) United States Patent
Chen et al.

(10) Patent No.: US 9,221,077 B2
(45) Date of Patent: Dec. 29, 2015

(54) CMUT ASSEMBLY WITH ACOUSTIC WINDOW

(75) Inventors: Li Chen, San Jose, CA (US); Yongli Huang, San Jose, CA (US)

(73) Assignee: Kolo Technologies, Inc., San Jose, CA (US)

( * ) Notice: Subject to any disclaimer, the term of this patent is extended or adjusted under 35 U.S.C. 154(b) by 904 days.

(21) Appl. No.: 13/467,638

(22) Filed: May 9, 2012

(65) Prior Publication Data

US 2013/0301394 A1 Nov. 14, 2013

(51) Int. Cl.
*H04R 17/00* (2006.01)
*B06B 1/02* (2006.01)
*G10K 11/18* (2006.01)
*G10K 11/32* (2006.01)

(52) U.S. Cl.
CPC ............. *B06B 1/0292* (2013.01); *G10K 11/18* (2013.01); *G10K 11/32* (2013.01)

(58) Field of Classification Search
CPC ....... B06B 1/0292; G01K 11/32; G01K 11/18
USPC ......................................... 367/155
See application file for complete search history.

(56) References Cited

U.S. PATENT DOCUMENTS

| | | | |
|---|---|---|---|
| 7,564,172 B1 | 7/2009 | Huang | |
| 8,018,301 B2 | 9/2011 | Huang | |
| 8,120,229 B2 | 2/2012 | Huang | |
| 8,299,550 B2 * | 10/2012 | Zaitsu et al. | 257/416 |
| 8,316,518 B2 * | 11/2012 | Lukacs et al. | 29/25.35 |
| 2007/0013269 A1 | 1/2007 | Huang | |
| 2008/0141521 A1 * | 6/2008 | Ladabaum et al. | 29/594 |
| 2009/0140606 A1 | 6/2009 | Huang | |
| 2010/0254222 A1 | 10/2010 | Huang | |
| 2010/0255623 A1 | 10/2010 | Huang | |
| 2010/0280388 A1 | 11/2010 | Huang | |
| 2011/0051554 A1 * | 3/2011 | Varray et al. | 367/87 |
| 2014/0204717 A1 * | 7/2014 | Kunkel et al. | 367/137 |

* cited by examiner

*Primary Examiner* — Mark Hellner
(74) *Attorney, Agent, or Firm* — Mattingly & Malur, PC

(57) ABSTRACT

In some implementations, a capacitive micromachined ultrasonic transducer (CMUT) apparatus includes one or more CMUTs or CMUT arrays, an acoustic window, a coupling medium, and a packaging substrate. The acoustic window may have various configurations, such as for reducing acoustic reflectance or increasing mechanical properties. In some examples, at least one of the CMUTs, the acoustic window or the coupling medium may include a focusing capability for focusing acoustic energy to or from the CMUT.

38 Claims, 18 Drawing Sheets

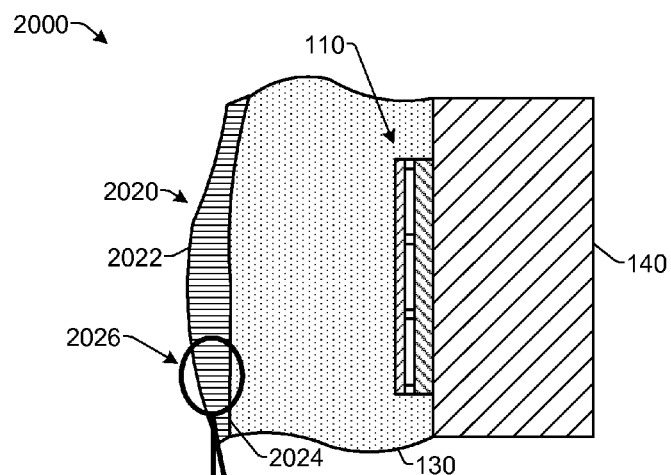
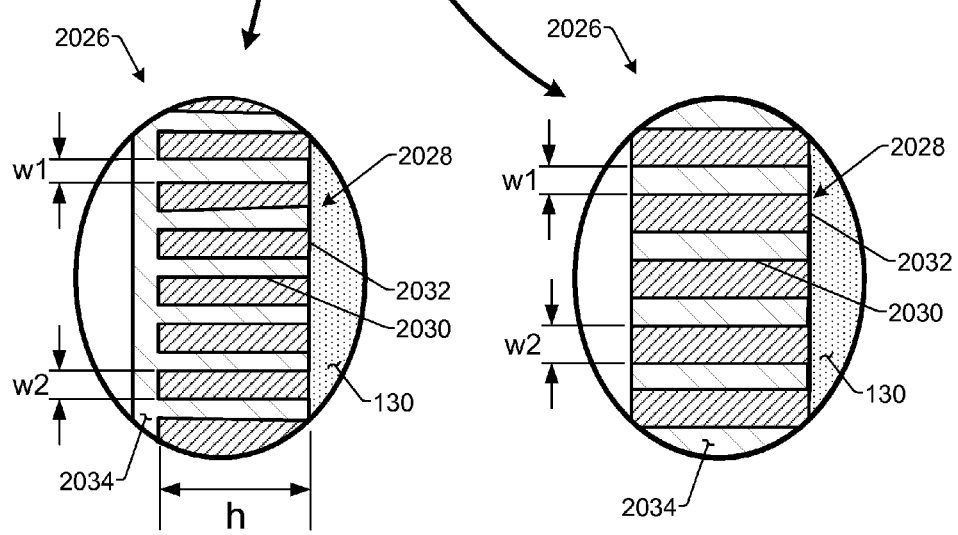
FIG. 20A
FIG. 20B   FIG. 20C

CMUT ASSEMBLY WITH ACOUSTIC WINDOW

TECHNICAL FIELD

Some implementations herein relate to acoustic transducers and transducer arrays, such as capacitive micromachined ultrasonic transducers (CMUTs) and CMUT arrays that may be employed with an acoustic window.

BACKGROUND

Electrostatic actuators and ultrasonic transducers may be used for various applications in a variety of media including liquids, solids and gas. For instance, ultrasonic transducers are commonly used in medical imaging, such as for diagnostics and therapy. Other uses may include biochemical imaging, non-destructive evaluation of materials, sonar, communications, proximity sensing, gas flow measurements, in-situ process monitoring, acoustic microscopy, underwater sensing and imaging, and numerous other practical applications.

A typical CMUT may include at least two electrodes with a transducing space (e.g., a separation gap) between the two electrodes that allows one of the electrodes to be physically displaced toward and away from the other electrode during operation. On the other hand, a typical piezoelectric transducer, such as those using lead zirconate titanate (PZT) may include a ceramic disc of piezoelectric material that develops a voltage across two of its faces when compressed (such as for sensor applications), or that physically changes shape when an external electric field is applied (such as for actuator applications including ultrasonic applications).

PZT transducers may sometimes be used with an acoustic lens that is placed on the front surface of the PZT transducer to shape the acoustic beam produced by the PZT transducer. A commonly used acoustic lens material for a PZT-based ultrasonic transducer in medical imaging is RTV silicone rubber (RTV). However, the acoustic loss in RTV may be significant, especially when the PZT transducer is operated at a relatively high frequency.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

FIGS. 20A-20C illustrate an example of a CMUT apparatus with an acoustic window having multiple layers of materials according to some implementations.

DETAILED DESCRIPTION

Figure 1A:
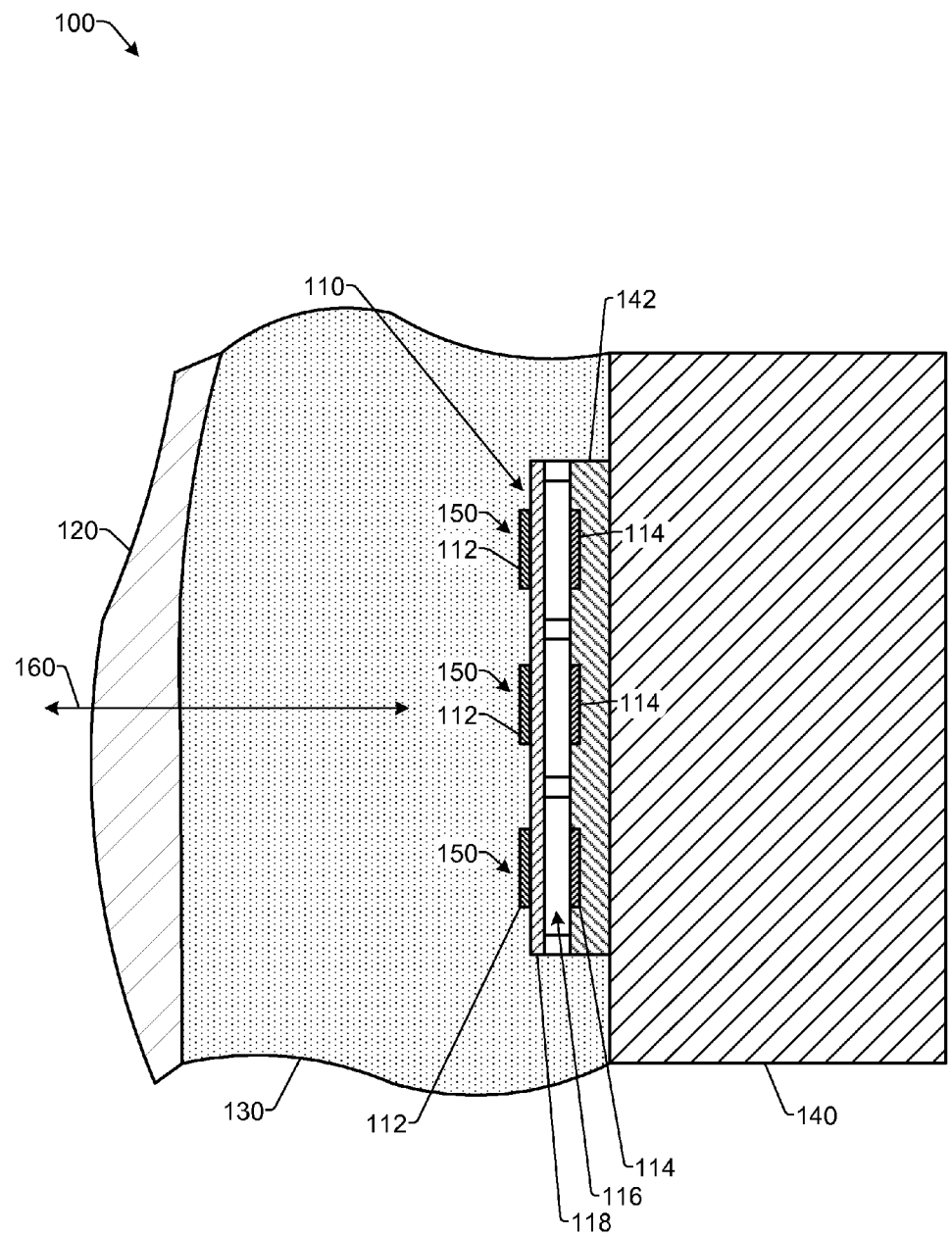
FIG. 1A illustrates a cross-sectional view of an example of a CMUT apparatus with an acoustic window according to some implementations.

This disclosure includes techniques and arrangements for a CMUT apparatus that may include an acoustic window. In some implementations, the CMUT (or the CMUT transducer elements of a CMUT array) may produce a focused acoustic output similar to what might be achieved through use of an acoustic lens. For example, through micromachining techniques, one or more CMUTs or one or more CMUTs as elements in an array can be constructed to have a desired shape to enable focusing of an acoustic beam transmitted by the CMUT(s). For instance, the CMUT in some implementations may be curved or otherwise shaped to focus emitted acoustic energy on a focal location and/or to achieve a desired acoustic beam profile. Thus, in some implementations, an acoustic lens may not be used or needed for focusing the acoustic beam. Accordingly, in the examples in which an acoustic lens is not used to focus the acoustic energy, the acoustic velocity or acoustic losses in the protection structure, such as those that may occur with RTV, are no longer a primary concern when designing a protective exterior contact surface or when selecting a material to use as the exterior contact material. Consequently, some implementations herein include a CMUT apparatus having an acoustic window that does not incur a substantial acoustic loss, unlike the lens materials commonly employed with PZT-based transducers.

In some examples, the acoustic window may have a substantially uniform thickness profile, i.e., a uniform thickness in cross section. The shape of the acoustic window with the uniform thickness profile can be flat, convex, concave, and so forth. The acoustic window can also be designed to have periodic or non-periodic shapes or patterns, while still having a uniform thickness. For example, the acoustic window may include at least one structural feature to reduce or minimize acoustic reflection. Additionally, in other implementations, the acoustic window may have a non-uniform thickness profile. For instance, the thickness profile can include multiple-step patterns or continually varied patterns. The pattern of the non-uniform thickness profile can be periodic or non-periodic, and the patterns may be designed or selected to minimize acoustic reflection. Further, the shape of the acoustic window with the non-uniform thickness profile (or pattern) can be flat (planar), convex, concave, or the like.

In some examples, the thickness profile of the acoustic window may be shaped as a convex lens or a concave lens so that the acoustic window may focus an acoustic output from the CMUT(s) or focus an acoustic input toward the CMUT(s). Further, periodic or non-periodic uneven surface patterns may be formed on the surface of the acoustic window to provide various effects on the acoustic energy, such as reducing reflection toward the CMUT(s). In some implementations, the acoustic window alone may provide a focusing functionality, while in other implementations, the coupling medium alone may provide a focusing functionality. In still other implementations, both the acoustic window and the coupling medium may together provide a focusing functionality, such as in the form of a compound acoustic lens. Additionally, in some examples, the acoustic window may have multiple layers, one or more coatings, and/or or one or more transition regions. The multiple layers, coatings or transition regions may have a thickness and/or impedance arranged to minimize acoustic reflection.

In one implementation, the CMUT array may include a common electrode for a plurality of CMUTs in the CMUT array. The common electrode may be close to or adjacent to a coupling medium and a protection layer may be formed on the CMUTs in the CMUT array. In some examples, the CMUTs may be coated with the protection layer so that one or more electrodes of the CMUTs do not directly contact the coupling medium, such as in the case in which the coupling medium is a conductive or semiconductive material. Thus, in some cases, the protection layer may insulate one or more CMUT electrodes from the coupling medium.

As mentioned above, a CMUT differs structurally from a PZT transducer, employs different construction materials, and may provide different acoustic properties. A basic structure of a PZT transducer may be a sandwich-type structure including a matching layer, a PZT layer and a backing layer. On the other hand, in some examples, a CMUT may be essentially constructed as a parallel capacitor with a movable electrode. Further, because the CMUTs herein typically have a much lower acoustic impedance than a PZT transducer, the CMUTs herein may not utilize or require a matching layer. The CMUTs herein may be fabricated on a CMUT substrate, such as silicon or other suitable substrate, and may be made flexible enough to form a curved shape to provide a focusing capability. Accordingly, the CMUT apparatuses herein may include CMUTs and CMUT arrays that are arranged to focus on an exterior focal location.

The CMUT apparatuses herein may be employed with any type of CMUT or array of CMUTs. For instance, there are many different possible CMUT designs (e.g., CMUT with flexible membrane, CMUT with embedded spring or surface plate, etc.), and accordingly, implementations herein are not limited to the particular CMUT structures shown and described. In the disclosure, a basic structure of a CMUT is used to illustrate the disclosed apparatus structures, arrangements and techniques, but the same apparatus structures, arrangements and techniques may be used in conjunction with any type of CMUT or CMUT array, including, but not limited to, flexible membrane CMUTs and embedded spring CMUTs (ESCMUTs), etc.

In some examples herein, a CMUT may include a first electrode and a second electrode separated from each other by a transducing space (or an electrode gap) so that a capacitance may exist between the electrodes. A spring member (e.g., a resilient flexible membrane or a spring layer) may support one of the electrodes to enable the two electrodes to move toward or away from each other. For instance, in a flexible membrane CMUT, the spring member may be a flexible membrane directly supporting one of the electrodes. Alternatively, in an ESCMUT, the spring member may be a spring layer supporting an electrode on a plate, which is suspended from the spring layer by spring-plate connectors. In addition, each CMUT may be made up of one or more CMUT cells. In some examples, multiple CMUT cells may make up a single CMUT and the cells may be of the same design as one another, or in other examples, the design of the cells may be different from one another.

In general, one CMUT or multiple CMUTs can be used to perform a function. In the case that multiple CMUTs are used, the multiple CMUTs may be arranged to form a CMUT array and each CMUT of the multiple CMUTs may be an element in the CMUT array. Thus, a CMUT array (e.g., a 1D, 1.5D, 1.75D, 2D array, etc.) can be formed by arranging multiple CMUTs in a pattern, such as in a line, in a grid, in cross pattern, and so forth. Implementations herein are not limited to any particular pattern or arrangement of CMUTs in a CMUT array. In some examples, each CMUT in the CMUT array may be a fully functional CMUT transducer that may be individually and independently addressable, i.e., an identifiable electrical output may be received therefrom or an identifiable electrical input may be provided thereto. Alternatively, in some examples, two or more CMUTs of multiple CMUTs included in a CMUT array may be commonly addressed CMUTs.

A CMUT or CMUT array may be packaged on a packaging substrate for mechanical support and/or to enable electrical connections. In some cases, the packaging substrate may be also used as an acoustic backing layer or may serve one or more other functions. The portion of the packaging substrate contacting the CMUT may be made of the material with high acoustic loss and the acoustic impedance close to that of the CMUT substrate, e.g. silicon or glass. In some examples, the packaging substrate may include some metal pads/traces (wires) for electrical connections, or may include a printed circuit board (PCB—e.g., flexible PCB, rigid PCB, or both) to electrically connect to the CMUT. Further, the packaging substrate may also be used to seal a coupling medium with other components in the CMUT apparatus.

In some examples, the CMUT apparatus may include the capability to control the shape or focus of the acoustic wave (or acoustic beam) output by the CMUT(s). This capability may be generally referred to herein as the focusing functionality or focusing capability. As one example, the shape or focus of the acoustic output may be controlled by shaping an active surface of the CMUT(s) into a desired curvature. As another example, the output may be focused by introducing a desired phase pattern (phase delay) in the acoustic wave generated by one CMUT. In still other examples, the shape or focus of the acoustic output may be controlled by an acoustic lens positioned in the front of the CMUT(s). In other examples, the some or all of the above techniques may be combined.

Example CMUT Apparatuses

FIG. 1A illustrates a cross-sectional view of an example CMUT apparatus 100 including an acoustic window according to some implementations. The CMUT apparatus 100 includes one or more CMUTs 110, which may be a single CMUT or multiple CMUTs, such as in a CMUT array. In this example, the CMUT 110 may include at least a first electrode 112 and a second electrode 114 positioned with respect to one another to form a transducing space 116 (i.e., an electrode separation gap between the two electrodes 112, 114). For example, the first electrode 112 may be mounted on a flexible membrane 118, a spring member, or the like, that may be displaced to change the transducing space 116.

As one example, in a transmission mode, an electric signal may cause a change in the transducing space 116 between the first electrode 112 and the second electrode 114 to cause acoustic output to be directed toward an acoustic window 120 through a coupling medium 130. Alternatively, in a reception mode, acoustic energy may pass through the acoustic window 120 and the coupling medium 130 to cause a change in the transducing space 116, thereby producing a signal indicative of the received acoustic energy. Further, implementations herein are not limited to any particular CMUT configuration, electrode locations, type of spring elements, flexible membrane arrangements, or the like. Additional non-limiting examples of suitable CMUTs and CMUT arrays that may be used with the acoustic windows and CMUT apparatuses herein are described in U.S. patent application Ser. No. 11/914,597, filed Feb. 12, 2009, and U.S. Pat. Nos. 7,564,172, 8,018,301, and 8,120,229, all to Yongli Huang, the entire disclosures of which are incorporated by reference herein.

In some examples, a protection layer (not shown in FIG. 1A) can be layered over an outer surface of the CMUT 110 to isolate the CMUT 110 and the electrodes 112, 114 from the coupling medium 130. The protection layer may be used if the coupling medium 130 is not non-conductive (e.g., conductive or semiconductive). The protection layer may be any suitable insulating or dielectric material, such as poly(p-xylylene) (e.g., Parylene®), polyimide, oxide, nitride, RTV, urethane, polyurethane, non-conductive polymer, or other suitable plastic or rubber materials.

The CMUT apparatus 100 may further include a CMUT packaging substrate 140, which, in some examples, may at least partially support the CMUT 110 and the coupling medium 130. For example, the CMUT 110 may be packaged on the packaging substrate 140. The packaging substrate 140 may provide electrical connections (not shown in FIG. 1A) to the first electrode 112 and the second electrode 114, as well as providing structural support to the CMUT 110 and the CMUT apparatus 100. The packaging substrate 140 may be of any suitable material, such as plastic, rubber, resin, metal, ceramic, or the like. An example of a typical packaging substrate for a CMUT includes at least a PCB (printed circuit board).

The packaging substrate 140 may support a CMUT substrate 142 that may be of silicon, glass or other suitable material for fabricating the one or more CMUTs 110. For example, one or more CMUT cells 150 of one or more CMUTs 110 may be deposited or otherwise built or positioned on the CMUT substrate 142. In some cases, there may be a plurality of CMUT cells 150 for each CMUT 110. Further, there may be a plurality of such CMUTs 110 built on the substrate 142 to form a 1D, 1.5D, 1.75D or 2D array of CMUTs.

Figure 1B:
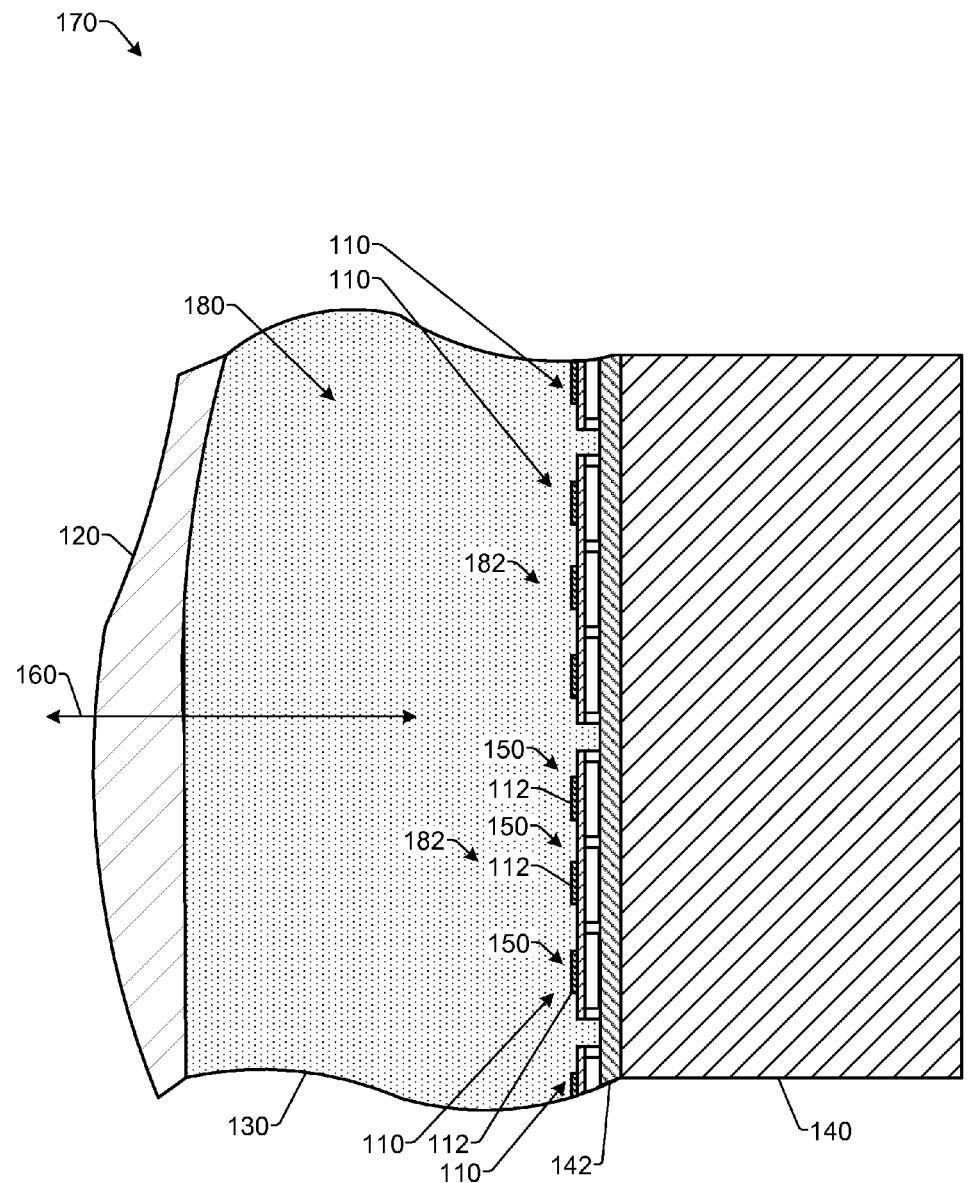
FIG. 1B illustrates a cross-sectional view of an example CMUT apparatus including a CMUT array and an acoustic window according to some implementations.

In some implementations, each CMUT cell 150 may include a first electrode 112 and a second electrode 114, as shown; however, in other implementations, some or all of the CMUT cells 150 may share common first and/or second electrodes (not shown in FIG. 1). Additionally, in some implementations, the first and second electrodes 112, 114 may be commonly addressed for the entire CMUT 110, i.e., they may share an electrical connection, or may be a single common electrode that extends across all the cells 150. In other implementations, however, one or both of the electrodes 112, 114 of each cell 150 may be individually addressed. In some cases, the cells 150 may be of the same or similar design; while in other cases, the cells 150 may be of two or more different designs in the same CMUT 110. Further, in some examples, as discussed below with respect to FIG. 1B, each CMUT 110 in a CMUT array may be separately addressable, such that individual CMUTs 110 in an array may be independently activated in transmission mode, or a signal may be independently detected therefrom in reception mode.

Further, the acoustic window 120 may wholly or partially enclose the coupling medium 130 to protect the one or more CMUTs 110 from directly contacting an external medium (not shown in FIG. 1A). The acoustic window 120 and the coupling medium 130 may also be configured or selected to effectively pass acoustic energy with minimal absorption or distortion. The acoustic window 120 is shown in the example of FIG. 1A having a random shape or thickness profile. Accordingly, in the example of FIG. 1A and in others of the following figures, except where specifically described otherwise, the acoustic window 120 may be an acoustic window of any suitable shape or thickness profile. For example, the acoustic window may be designed to have a desired shape and thickness profile to achieve desired mechanical and acoustic properties, as discussed additionally below.

In some examples, the acoustic window 120 may be solid material that is able to provide protection mechanically for the CMUT apparatus 100. The thickness of the acoustic window 120 may be thin enough to have minimum internal acoustic loss, but thick enough to protect the CMUT apparatus 100 during use, such as when contacting an external medium. In some examples, the acoustic window 120 may have a thickness in the range of 0.1 to 20 wavelengths of the acoustic wave in the frequency at which the CMUT 110 operates. Accordingly, the acoustic window 120 may be structurally strong enough to be pressed against an external medium, such as when the CMUT apparatus is part of a medical probe or other instrument.

For medical imaging applications, suitable materials for the acoustic window 120 include, but are not limited to, plastics and rubber material, such as polyethylene or polyurethane formulations, polymethylpentene, acrylonitrile butadiene styrene (ABS), polycarbonate ABS (PC-ABS), thermoplastic polycarbonate (e.g., Makrolon®), polysulfone, cross-linked polystyrene microwave plastic (e.g., Rexolite®), polyamides, and so forth. In some examples, the material of the acoustic window 120 may be chosen to have an acoustic property, such as an acoustic impedance, that matches (i.e., the same, similar or close to) the acoustic properties (e.g., acoustic impedance) of the intended or targeted external medium (e.g. human tissue, which has acoustic impedance about 1.5 MRayl). For example, if the external medium is human tissue, the acoustic impedance of the acoustic window may be chosen in the range of 1-4 MRayl. In more specific examples, the acoustic impedance of the acoustic window may be chosen in a range of 1.5+/−0.5 MRayl. In other examples, such as for other applications of the CMUT apparatuses herein, a suitable material for the acoustic window 120 may have an acoustic impedance that closely matches that of other respective target external media, such as within the same order of magnitude or less. Further, the acoustic impedance of the acoustic window 120 may be the same as, or close to, that of the coupling medium 130 (e.g., in the same ranges as discussed above) in addition to that of the target medium (e.g., human tissue, etc.) outside the CMUT apparatus 100. If the impedance of the acoustic window has a relatively large mismatch with the intended or targeted external medium or the coupling medium 130, then one or more additional (matching) layer(s) or transition layer(s) may be built on the acoustic window, As discussed additionally below, the acoustic window 120 and/or the coupling medium 130 in some examples may not need to have a focusing capability. Therefore, more materials are available to be used for the acoustic window 120 and coupling medium 130 than if an acoustic lens is used as the acoustic window 120 with the CMUT apparatus 100. Additionally, in some examples, an acoustic lens (e.g., made of RTV or made from other material listed above) can also be included with the acoustic window 120 on the CMUT apparatus 100.

The coupling medium 130 serves to couple acoustic energy, such as an acoustic wave, between the CMUT 110 and the acoustic window 120. The coupling medium 130 can be liquid-based, solid-based, or gel-based, etc. The coupling medium may have a low acoustic loss and an acoustic impedance that matches with that of CMUT 110 and/or the acoustic window 120. Accordingly, the coupling medium 130 may be selected to have a minimum impact on both the acoustic energy transfer and the frequency response of the CMUT apparatus 100. Furthermore, in some examples, if the coupling medium is solid-based, the coupling medium may have a Young's modulus smaller than 5 GPa. In more specific examples, the coupling medium may have a Young's modulus smaller than 1 GPa.

Additionally, in some examples, the coupling medium 130 may not be non-conductive material (e.g., the coupling medium 130 may be conductive). In these cases, a ground electrode (GND) of the CMUT (e.g., the first electrode 112) may be designed to face and contact the coupling medium 130, while a second electrode (e.g., second electrode 114) may be insulated from the coupling medium 130. For instance, for a CMUT array that has a common electrode among multiple CMUT elements, the common electrode of the CMUT elements is typically also the ground electrode (GND) of the CMUT elements.

Some example solid-based materials suitable for the coupling medium 130 include, but are not limited to, plastics and rubber material, polydimethylsiloxane (PDMS), poly(p-xylylene) (e.g., Parylene®), RTV, silicone (e.g. PDMS), nitride, oxide, Riston® dry film photoresist, polyimide films (e.g., Kapton®), photoresist, polyimide, urethane, polyurethane, cross-linked polystyrene microwave plastic (e.g., Rexolite®), polyethylene, other polymers, and so forth.

Additionally, materials used for the coupling medium 130 may be liquid-based, such as water-based, gel-based, oil-based, or synthetic polymeric liquids, etc. Some example suitable liquid-based materials for the coupling medium 130 include, but are not limited to, methyl salicylate, giycol, silicone gel, methylsilicone oil, mixtures of water and gilycol, and the like. In addition, the materials may be chosen from the group consisting of liquid, a gel and a colloid. Examples of liquids include, without limitation, water, a saline solution, glycerol, castor oil, mineral oil, vegetable oil and fluorocarbon-based fluid (e.g., Fluorinert®), and the like. Moreover, in some examples, the coupling medium 130 may be a mixture of 1-Butanol in Glycerol. For instance, the attenuation of the mixture may be adjusted without impairing acoustic velocity matching by adding a suitable amount of 2-Hydroxyethyl ether.

Acoustic energy, such as an acoustic beam, may pass through the acoustic window 120 and the coupling medium 130 in an operational direction 160 to or from the one or more CMUTs 110. For example, in a transmission mode, the CMUT 110 or the CMUT array may emit acoustic energy toward the acoustic window 120, generally in the operational direction 160. Similarly, in a reception mode, the CMUT 110 or the CMUT array may receive acoustic energy passing through the acoustic window 120 and the coupling medium 130 in the operational direction 160.

The thickness of the coupling medium 130 may be thin enough to have minimum internal acoustic loss, but thick enough to serve as a buffer layer between the acoustic window 120 and the CMUT 110 so that the properties of the selected acoustic window 120 has a minimum impact on the performance of the CMUT 110. In some examples, the thickness of the coupling medium 130 may be larger than ¼ of the wavelength of the acoustic wave in the frequency at which the CMUT operates.

FIG. 1B illustrates an example CMUT apparatus 170 including the acoustic window 120 and a CMUT array 180 according to some implementations. For instance, in some cases, the CMUT apparatus may include a single CMUT 110 while, in other cases, the CMUT apparatus may include multiple CMUTs 110. In some examples, the multiple CMUTs 110 may be configured into an array, such as the CMUT array 180, with each CMUT 110 serving as an element of the CMUT array 180. In the illustrated example, the CMUT array 180 includes a plurality of the CMUTs 110 described above with respect to FIG. 1A. The CMUT array 180 may be any suitable array configuration, such as a 1D, 1.25D, 1.5D, 1.75D, 2D array, or the like. For example, the CMUT array 180 may have a linear pattern, a two-dimensional array pattern, such as a grid pattern, a cross pattern, or any other desired arrangement. Thus, implementations are not limited to any particular array configuration.

In the example of FIG. 1B, the substrate 142 may be conductive and, therefore, may serve as a common electrode for multiple CMUTs 110. The first electrodes 112 may be individually addressable for each CMUT 110 or, alternatively, may be individually addressable for each cell 150 of each CMUT 110. As another alternative, rather than having the substrate 142 be conductive, the second electrodes 114 may be included in the CMUTs 110 in the example of FIG. 1B, similar to the example, described above with respect to FIG. 1A. Other variations will also be apparent to those of skill in the art in light of the disclosure herein.

In the illustrated example, the CMUT array 180 is formed on a flat CMUT substrate 142 and a flat packaging substrate 140. Thus, the CMUTs 110 of the CMUT array 180 have active surfaces 182 facing in the operational direction 160, and may operate in the operational direction 160 to transmit and/or receive acoustic energy through the acoustic window 120 and coupling medium 130. Thus, the active surface 182 of a CMUT 110 may serve to receive acoustic energy in receiving mode or generate acoustic energy in a transmission mode. In other examples, the CMUT substrate 142 and/or the packaging substrate 140 may be curved to form the curved active surface for a CMUT 110, thus to have focus capability. For example, a concave curve may at least in part focus each CMUT 110 in the CMUT array 180 toward a particular focal locations, while a convex curve may at least in part focus the CMUT 110 in a disparate direction.

Figure 2:
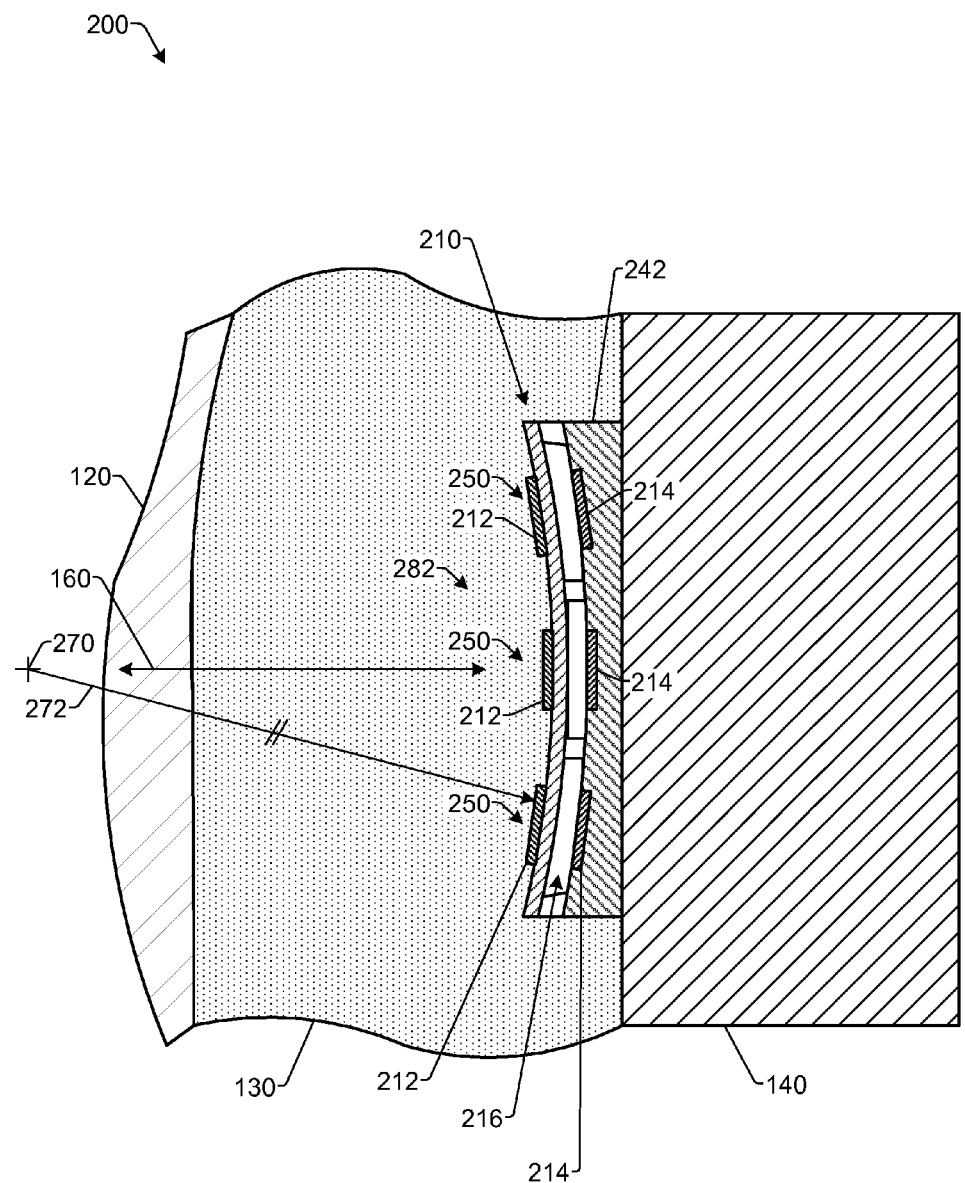
FIG. 2 illustrates a cross-sectional view of an example of a CMUT apparatus with an acoustic window and a CMUT (or CMUT array) having a focusing capability according to some implementations.

FIG. 2 illustrates a cross-sectional view of an example CMUT apparatus 200 having an acoustic window according to some implementations. The CMUT apparatus 200 includes one or more CMUTs 210 (which may include one or more CMUT arrays) with focusing capability. The CMUT apparatus 200 further includes the acoustic window 120, the coupling medium 130 and the CMUT packaging substrate 140. The CMUT 210 may include at least two electrodes, such as a first electrode 212 and a second electrode 214 separated by a transducing space 216, which operate similarly to the CMUT 110 discussed above. For instance, the CMUT 210 may include a plurality of CMUT cells 250, each of which may include a first electrode 212 and a second electrode 214.

Furthermore, in some implementations, the CMUT 210 may be part of a CMUT array including a plurality of CMUTs 210, similar to the example described above with respect to FIG. 1B. In the case in which the CMUT 210 is included in a CMUT array, the CMUT 210 may include individual electrodes, such as the first and second electrodes 212, 214, or may include one or more common electrodes shared with one or more other CMUTs 210 in the CMUT array. For example, the CMUTs 210 in a CMUT array may share one common electrode as a first electrode and have individual independently addressable electrodes as a second electrode, as discussed above with respect to FIG. 1B, and as discussed additionally below.

In some cases, the CMUT apparatus 200 may include a focusing capability to shape the acoustic output of the CMUT 210. For example, if the acoustic window 120 and the coupling medium 130 do not have a focusing functionality, the CMUT 210 may be designed to have focusing capability to focus the acoustic energy at a focal area or focal location 270. For instance, the CMUT 210, which may include a CMUT substrate 242, may be formed or shaped such that an active surface 282 of the CMUT 210 has a desired shape or curvature 272 to achieve a desired focus function generally in the operational direction 160 for focusing the acoustic energy at the focal location 270. Additionally, in other examples, an acoustic lens that also includes focusing capability may also be incorporated into at least one of the acoustic window 120 or the coupling medium 130 to provide additional focusing capability.

Alternatively, a CMUT or CMUTs in a CMUT array (i.e., including either the CMUT 110 having a generally flat configuration, or a CMUT 210 having a curved configuration) may be configured or operated to have an acoustic output with a desired non-uniform phase pattern, amplitude pattern, or both. For example, the flat or curved CMUT 110, 210, respectively, discussed herein, or the CMUTs 110, 210 configured in CMUT arrays, may be operated to focus on a desired focal location 270. Thus, by introducing a phase difference (e.g., a 180 degree phase difference) into the distribution for the acoustic wave emitted by various CMUT cells 150, 250 at different locations in a CMUT 110, 210, the acoustic wave intensity can be enhanced at one or more particular focal areas or focal locations 270, even though the CMUT itself is flat (CMUT 110) or of a fixed curvature (CMUT 210), Accordingly, by controlling the operation phase and/or amplitude distribution of individual CMUT cells in a CMUT or individual CMUTs in a CMUT array, the ultrasonic energy may be focused to a certain extent even though the acoustic source is flat or of a fixed curvature.

In the following examples, except when specifically mentioned, the CMUTs and/or CMUT arrays in the CMUT apparatuses described in the following implementations, may or may not have focusing capabilities. In addition, while a single CMUT 110 or 210 may be shown in the examples, it is to be understood that the CMUT 110, 210 in the examples may, in some cases, be only one element of a larger CMUT array including a plurality of CMUTs 110 and/or 210. Further, other types of CMUTs may be used in the examples herein or intermixed with one another in the arrays herein in addition to, or as an alternative to, the CMUTs 110, 210 described in the examples herein.

Figure 3:
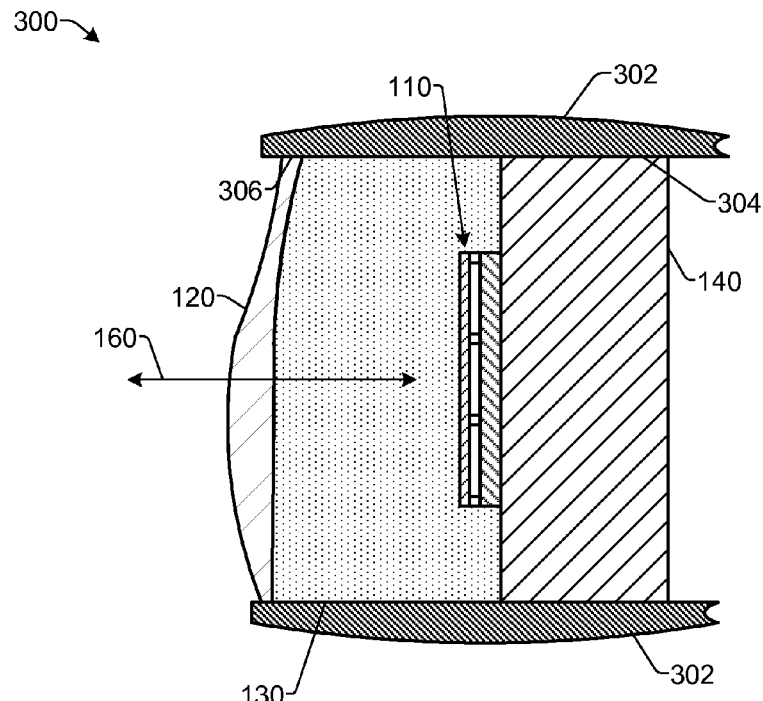
FIG. 3 illustrates a cross-sectional view of an example of a CMUT apparatus with an acoustic window and a sealed coupling medium according to some implementations.

FIG. 3 illustrates a cross-sectional view of an example of a CMUT apparatus 300 with the acoustic window 120 and a sealed coupling medium 130. For example, in the situation that the coupling medium 130 is a liquid-based or gel-based material, the coupling medium 130 may be enclosed in a sealed space. Accordingly, a case or housing 302 may be used to seal the coupling medium 130 with the acoustic window 120, CMUT packaging substrate 140, the CMUT 110 or 210 and any other components.

In the example of FIG. 3, the housing 302 may enclose and contain or retain the coupling medium 130 and the CMUT 110. A first seal 304 may be formed between the housing 302 and the packaging substrate 140, and a second seal 306 may be formed between the housing 302 and the acoustic window 120. The seals 304, 306 may be formed using any suitable technology, such as adhesion material (e.g., epoxy, glue, etc.), O-rings, molding, (thermal) compression, interference fit, shrink fit, bonding without adhesive, magnetic attraction, electro-static attraction, or any other suitable sealing technique. The sealing can be also engineered to provide acoustic decoupling between different components at the seal location.

Figure 4:
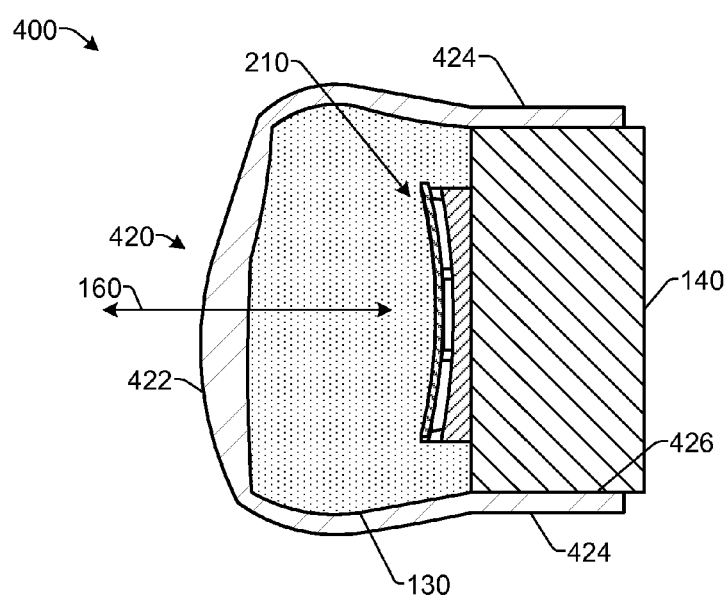
FIG. 4 illustrates a cross-sectional view of an example of a CMUT apparatus with an acoustic window and a sealed coupling medium according to some implementations.

FIG. 4 illustrates a cross-sectional view of an example CMUT apparatus 400 with an acoustic window 420 and sealed coupling medium 130 according to some implementations. In this example, the material of the acoustic window 420 itself may be used to contain the coupling medium 130. For instance, the acoustic window 420 may be formed to include a front or window portion 422 and sidewall(s) 424. Accordingly, the acoustic window 420 may also serve as a housing for enclosing and containing the coupling medium 130 in contact with the other components such as the CMUT 110 or 210 and the packaging substrate 140.

In the illustrated example, the CMUT apparatus 400 includes the CMUT 210, the acoustic window 420, the coupling medium 130, and the CMUT packaging substrate 140. The acoustic window 420 serves at least two functions: (1) an acoustic window function, which is served by the window portion 422, and (2) a packaging function, which is served by the sidewall(s) 424. Thus, the window portion 422 is used to pass acoustic energy to or from the CMUT 210 in the operational direction 160. The sidewalls 424 are not used to pass usable acoustic energy, but instead serve to enclose or seal the coupling medium and retain the coupling medium 130 with the other components, such as the CMUT 210 and the substrate 140. Thus, a seal 426 may be formed between the sidewall(s) 424 and the packaging substrate 140. Compared with the implementation 300 discussed above with respect to FIG. 3, one of the sealing interfaces, i.e., second seal 306 may be eliminated during the assembly process in the implementation of FIG. 4. The seal 426 may be formed using any suitable technique, such as those discussed above with respect to FIG. 3.

FIGS. 5-20 provide several examples of acoustic windows and coupling media according to some implementations. For clarity of illustration, a housing or other enclosure or retaining structure is not shown in FIGS. 5-20. However, any of the sealing and retaining techniques described above such as those described in FIGS. 3-4, or others, may be used in any of the implementations herein.

Figure 5:
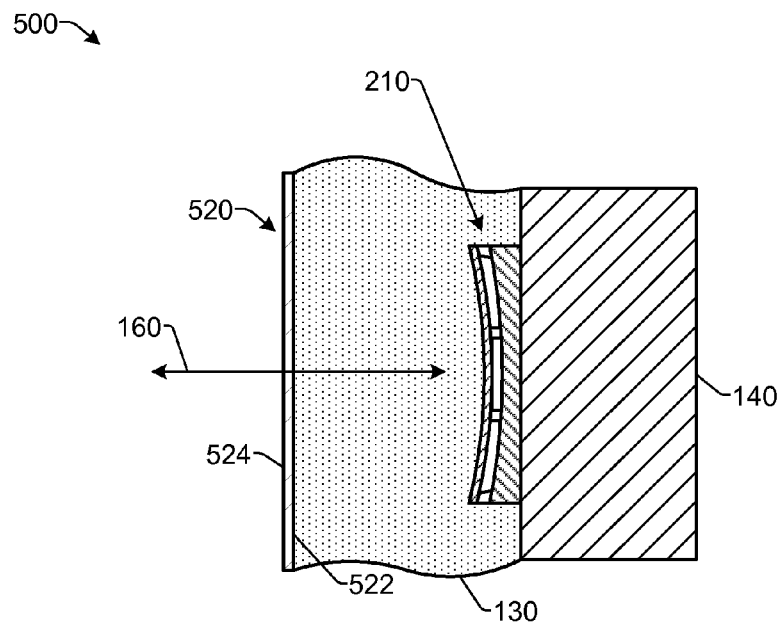
FIG. 5 illustrates a cross-sectional view of an example of a CMUT apparatus with an acoustic window having a planar shape and a uniform thickness profile according to some implementations.

FIG. 5 illustrates a cross-sectional view of an example of a CMUT apparatus 500 with an acoustic window 520 according to some implementations. The CMUT apparatus 500 may include a CMUT (or a CMUT array), such as the CMUTs 110 or 210 discussed above. In the illustrated example, the CMUT apparatus 500 includes the CMUT 210, the acoustic window 520, the coupling medium 130, and the CMUT packaging substrate 140. The acoustic window 520 may have a flat or planar configuration with a uniform thickness profile in cross section. In order to minimize acoustic reflection (e.g., at a transition or interface 522 between the coupling medium 130 and the acoustic window 520, or at the interface 524 between the acoustic window 520 and an external medium (e.g., air, tissue, etc.), the acoustic impedances of the acoustic window 520 and the coupling medium 130 may be selected to be close to the impedance of the target medium (e.g., human tissue in some examples).

In some cases, when there is an acoustic impedance mismatch among the acoustic window 520, the coupling medium 130 and/or the target medium, the thickness of both the acoustic window 520 and the coupling medium 130 may be selected to minimize the acoustic reflection from the acoustic window 520. One example technique to minimize acoustic reflection is to have the reflected waves from the different interfaces 522, 524 at least partially cancel out each other. For example, in the case of an impedance mismatch among the acoustic window 520, the coupling medium 130 and the target medium, the thickness of the acoustic window 520 or the coupling medium 130, or both, may be ¼ or ½ of the acoustic wavelength, or multiples of ¼ or ½ of the acoustic wavelength, of the acoustic frequency at which the CMUT 210 operates. This thickness selection can potentially minimize the acoustic reflection. Further, since the flat acoustic window 520 does not provide a focusing capability (or lens function), the CMUT 210 may provide a focusing capability, as discussed above, if it is desired to focus the CMUT apparatus 500 on a particular focal location or focal area.

Figure 6:
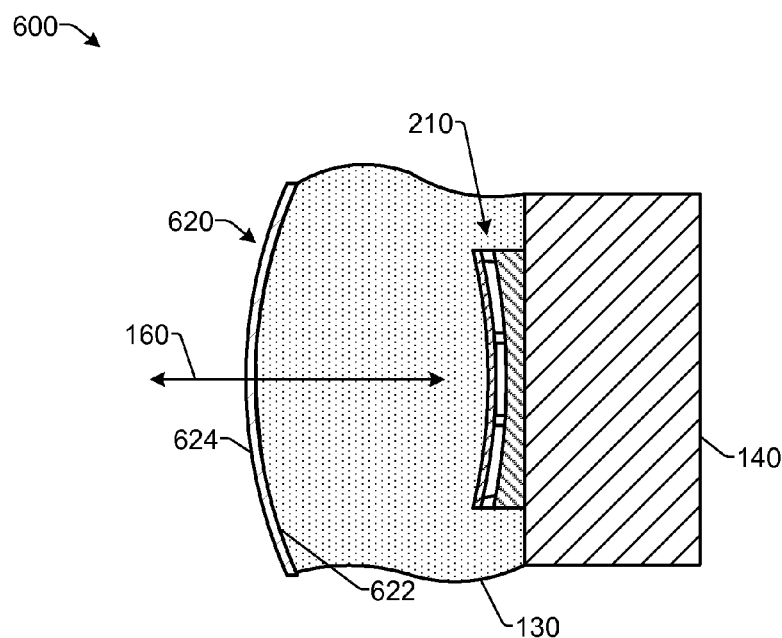
FIG. 6 illustrates a cross-sectional view of an example of a CMUT apparatus with an acoustic window having a convex shape and a uniform thickness profile according to some implementations.

FIG. 6 illustrates a cross-sectional view of an example CMUT apparatus 600 with an acoustic window 620 according to some implementations. The CMUT apparatus 600 may include a CMUT (or a CMUT array), such as the CMUTs 110 or 210 discussed above. In the illustrated example, the CMUT apparatus 600 includes the CMUT 210, the acoustic window 620, the coupling medium 130, and the CMUT packaging substrate 140. The acoustic window 620 may have an overall convex shape facing outward from the CMUT 210 and a uniform thickness profile. In this example, there may be less reflection from an interface 622 of acoustic window 620 with the coupling medium 130 and/or an interface 624 of the acoustic window 620 with the target medium than in the implementation of FIG. 5. However, both the acoustic impedances and the thicknesses of the acoustic window 620 and the coupling medium 130 may be selected the same way as that described for the CMUT apparatus 500 having the flat acoustic window 520 illustrated in FIG. 5.

Further, in this example, in the case that the velocity of the acoustic wave or acoustic energy in the coupling medium 130 is different from (e.g., slower than) that in the outside target medium, the coupling medium 130 may provide a focusing capability and may serve as a de facto acoustic lens. Therefore, in some examples, the CMUT used might not have a focusing capability. For example, the CMUT 110 or other non-focused transducer may be used, rather than a focused transducer, such as the CMUT 210.

Figure 7:
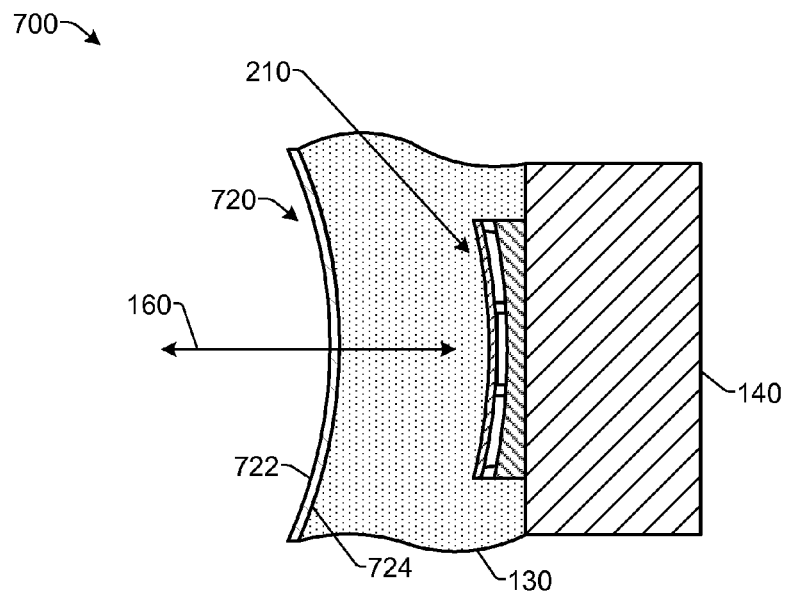
FIG. 7 illustrates a cross-sectional view of an example of a CMUT apparatus with an acoustic window having a concave shape and a uniform thickness profile according to some implementations.

FIG. 7 illustrates a cross-sectional view of an example CMUT apparatus 700 with an acoustic window 720 according to some implementations. The CMUT apparatus 700 may include a CMUT (or a CMUT array), such as the CMUTs 110 or 210 discussed above. In the illustrated example, the CMUT apparatus 700 includes the CMUT 210, the acoustic window 720, the coupling medium 130, and the CMUT packaging substrate 140. The acoustic window 720 has a concave shape facing outward from the CMUT 210 in the operational direction 160, and a uniform thickness profile. In this example, there may be less reflection from and interface 722 of the acoustic window 720 with the target medium and/or an interface 724 of the acoustic window 702 with the coupling medium 130 than in the implementation of FIG. 5. However, both the acoustic impedances and the thicknesses of the acoustic window 720 and the coupling medium 130 may be selected the same way as that described above for the CMUT apparatus 500 having the flat acoustic window 520 shown in FIG. 5.

Further, in the case that the acoustic velocity of the acoustic wave in the coupling medium 130 is different from (e.g., faster than) that in the external target medium, the coupling medium 130 may have a de facto focusing capability and may serve as a lens. Therefore, the CMUT used might not have a focusing capability. For example, the CMUT 110 may be used in the CMUT apparatus 700.

Figure 8:
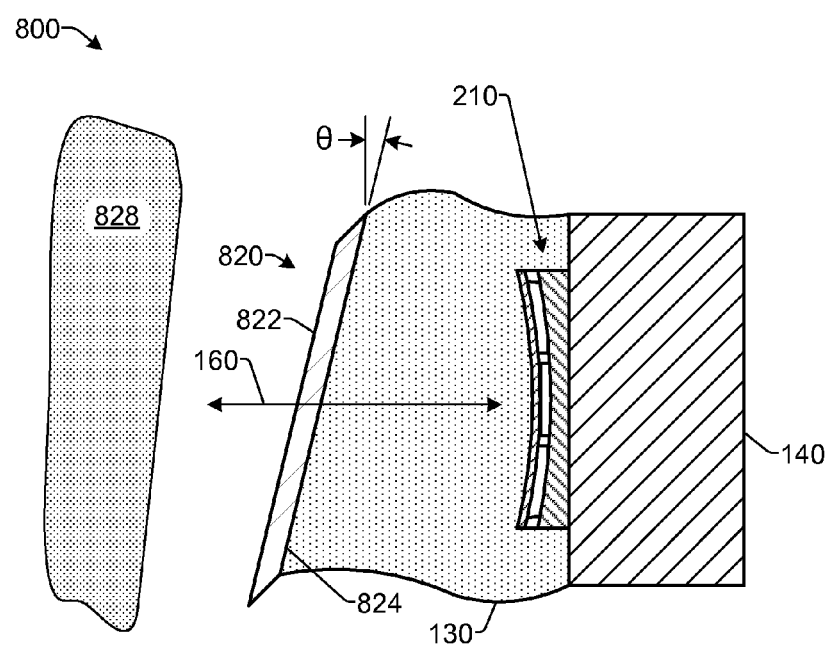
FIG. 8 illustrates a cross-sectional view of an example of a CMUT apparatus with an acoustic window having a tilted planar configuration and a uniform thickness profile according to some implementations.

FIG. 8 illustrates a cross-sectional view of an example CMUT apparatus 800 with an acoustic window 820 according to some implementations. The CMUT apparatus 800 may include a CMUT (or a CMUT array), such as the CMUTs 110 or 210 discussed above. In the illustrated example, the CMUT apparatus 800 includes the CMUT 210, the acoustic window 820, the coupling medium 130, and the CMUT packaging substrate 140. The acoustic window 820 may have a flat outer face 822, a flat inner face 824, and may have a uniform thickness. Further, the acoustic window 820 may form a plane that is tilted at an angle θ with respect to the CMUT 210 and the operational direction 160. For example, the outer face 822, the inner face 824, or another portion of the acoustic window 820 may generally form an overall plane or a major plane that is tilted at the angle θ with respect to the operational direction 160 of the CMUT 210. For example, the operational direction 160 may generally include the direction in which the one or more CMUTs 210 emit acoustic energy and/or the direction from which the one of more CMUTs 210 are positioned to effectively receive acoustic energy. Also, FIG. 8 shows that the acoustic window 820 is tilted with respect to the CMUT 210; however, the tilting between the CMUT 210 and the acoustic window 820 may be relative to one another in FIG. 8, e.g. the configuration have the same effect if the CMUT 210 is tilted with respect to the acoustic window 820.

Accordingly, acoustic energy, such as an acoustic beam that passes through the acoustic window 820 will pass through in the operational direction 160 at a non-perpendicular or oblique angle based at least in part on the angle of tilt θ of the plane of the acoustic window 820. For example, in transmission mode, the one or more CMUTs 210 may emit acoustic energy toward the acoustic window 820, generally in the operational direction 160. Similarly, in reception mode, the one or more CMUTs 210 may receive acoustic energy passing through the acoustic window 820 in the operational direction 160. Accordingly, the positioning of the acoustic window 820 at the angle θ with respect to the operational direction 160 of travel of the acoustic energy can further reduce the reflection from the acoustic window 820.

The tilt angle θ may be selected to direct any reflected acoustic energy away from the CMUT 210, and may have a minimum impact on the shape and direction of the acoustic energy that passes through the acoustic window 820. Moreover, both the acoustic impedances and the thicknesses of the acoustic window 820 and the coupling medium 130 may be selected in a manner similar to that described above with respect to the CMUT apparatus 500 with the flat acoustic window 520 of FIG. 5. Additionally, since the flat acoustic window 820 does not have a focusing capability (or a lens function), the CMUT 210 may include a focusing capability if it is desired to focus the CMUT apparatus 800.

If the acoustic transmission properties (e.g., acoustic velocity or acoustic impedance) of the coupling medium 130 and/or that of an outside target medium 828 are substantially different from that of the acoustic window 820 at the operation frequency of the CMUT 210, then the acoustic beam may be steered or refracted away from its original direction during passage through an interface between the inner face 824 and the coupling medium 830 and/or during passage through an interface between the outer face 822 and the outside target medium 828 (e.g., human tissue in the case of a medical probe). If this refractive effect is desired to be avoided, an alternative configuration of the acoustic window may be used, such as the configurations of FIG. 9 or 10.

Figure 9:
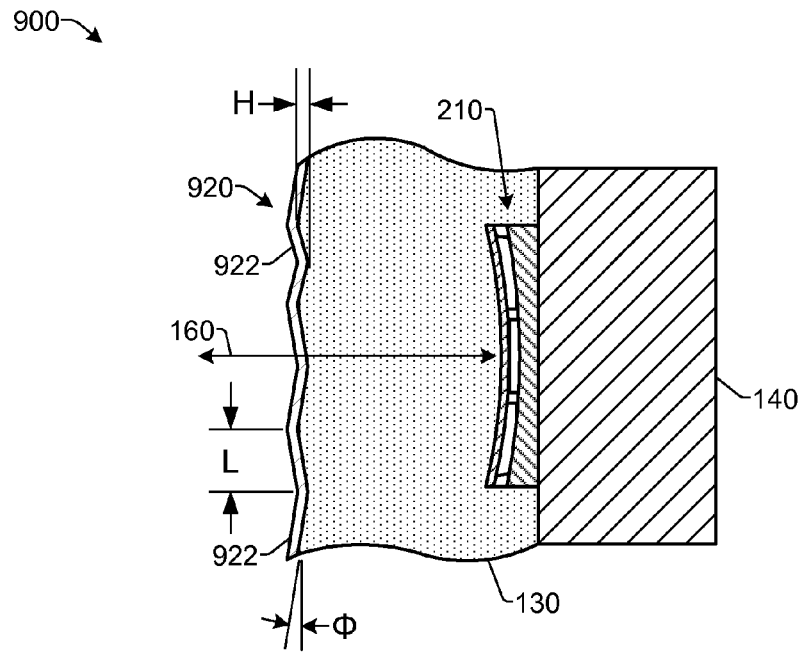
FIG. 9 illustrates a cross-sectional view of an example of a CMUT apparatus with an acoustic window having multiple tilted facets and a uniform thickness profile according to some implementations.

FIG. 9 illustrates a cross-sectional view of an example of a CMUT apparatus 900 with an acoustic window 920 according to some implementations. The CMUT apparatus 900 may include a CMUT (or a CMUT array), such as the CMUTs 110 or 210 discussed above. In the illustrated example, the CMUT apparatus 900 includes the CMUT 210, the acoustic window 920, the coupling medium 130, and the CMUT packaging substrate 140. The acoustic window 920 may include a uniform thickness profile; however, instead of tilting a flat-plate or planar acoustic window, as described above with respect to FIG. 8, in this implementation, the acoustic window 920 may include a plurality of tilted or angled facets 922. The angle Φ of tilt of the facets 922 may be selected to reduce the reflection from the acoustic window 920 to the CMUT 210. The geometric size of the facets 922 may be designed in a range of 0.1 times to 10 times of the acoustic wavelength at which the transducer operates. For example, the range of the height H of the facets 922 may be selected to be in a range of 0.1 times to 1 times of the acoustic wavelength generated by the CMUT 210. Further, the range of the length L of the facets 922 may be selected to be in a range of 0.25 times to 10 times of the acoustic wavelength generated by the CMUT 210.

In addition, FIG. 9 illustrates a cross section of the window 920, showing the facets in a first direction. In some examples, the facets 922 may be longitudinal parallel facets that tilt in alternate direction by the angle Φ. In other examples, the facets 922 may be formed in two directions, such as in the shape of a plurality adjacent pyramids. Additionally, in the illustrated example, the facets 922 may be designed as the periodic pattern of alternating angles of tilt, as shown in FIG. 9. Alternatively, the facets 922 may be designed as non-periodic patterns with different heights, lengths and/or angles of tilt among the plurality of facets 922.

Figure 10:
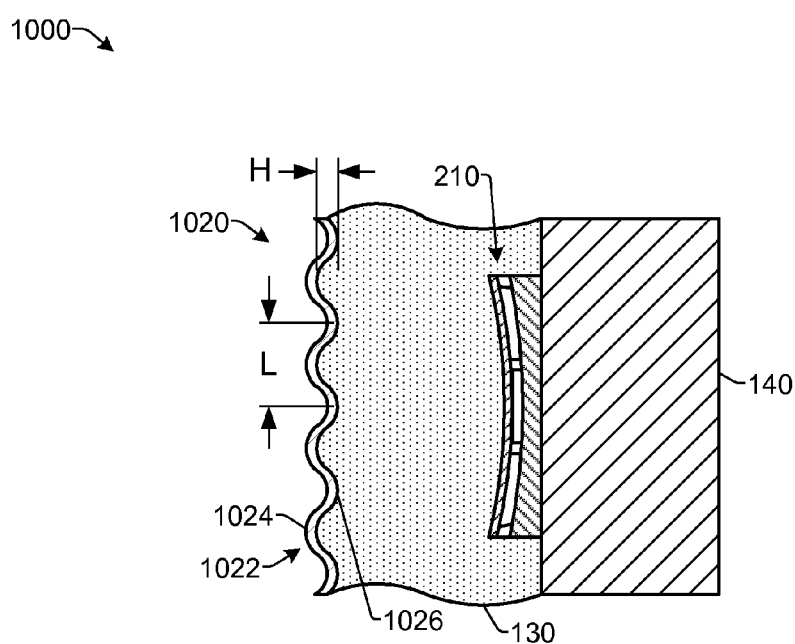
FIG. 10 illustrates a cross-sectional view of an example of a CMUT apparatus with an acoustic window having gradually varied patterns or undulations and a uniform thickness profile according to some implementations.

FIG. 10 illustrates a cross-sectional view of an example CMUT apparatus 1000 with an acoustic window 1020 according to some implementations. The CMUT apparatus 1000 may include a CMUT (or a CMUT array), such as the CMUTs 110 or 210 discussed above. In the illustrated example, the CMUT apparatus 1000 includes CMUT 210, the acoustic window 1020, the coupling medium 130, and the CMUT packaging substrate 140. The acoustic window 1020 may have a uniform thickness profile. Further, rather than having many facets with tilted flat surfaces as illustrated in FIG. 9, the acoustic window 1000 may be undulated into continuously curved patterns 1022 to effectively reduce the reflection to the CMUT 210 from the acoustic window 1020. For example, the curved or undulating patterns 1022 may be formed as a sine wave or other gradually changing shapes having a series of peaks 1024 and valleys 1026 with respect to at least one direction. The geometric size of the patterns 1022 may be selected to be in a range of 0.1 times to 10 times of the acoustic wavelength at which the CMUT 210 operates. For example, the range of the height H of the patterns 1022 may be selected to be in a range of 0.1 times to 1 times of the acoustic wavelength that the CMUT 210 generates. Further, the range of the length L (e.g., from one valley to the next valley or from one peak to the next peak) of the patterns 1022 may be selected to be in a range of 0.25 times to 10 times of the acoustic wavelength generated by the CMUT 210. The patterns 1022 of the acoustic window can be designed as regular or periodic patterns as shown in FIG. 10. In some cases, the pattern 1022 of undulations may be formed in one direction as a plurality of generally parallel elongated peaks 1024 and channels or valleys 1026, giving the acoustic window 1020 a corrugated surface pattern. In other examples, the pattern of undulations may be formed in two directions providing a plurality of individual peaks 1024 surrounded by valleys 1026 on all sides. As still another example, the patterns 1022 may be designed as non-periodic patterns with different heights and/or lengths. As still another example, the non-periodic pattern may extend in only one direction or may extend in two directions across the acoustic window 1020.

Furthermore, rather than the acoustic windows having a uniform thickness profile, such as are illustrated in FIGS. 5-10, the acoustic windows herein may have a non-uniform thickness profile or cross sectional thickness to achieve one or more desired acoustic effects. FIGS. 11-17 illustrate some example implementations of acoustic windows having a non-uniform cross sectional thickness, such as having at least two portions with different thicknesses.

Figure 11:
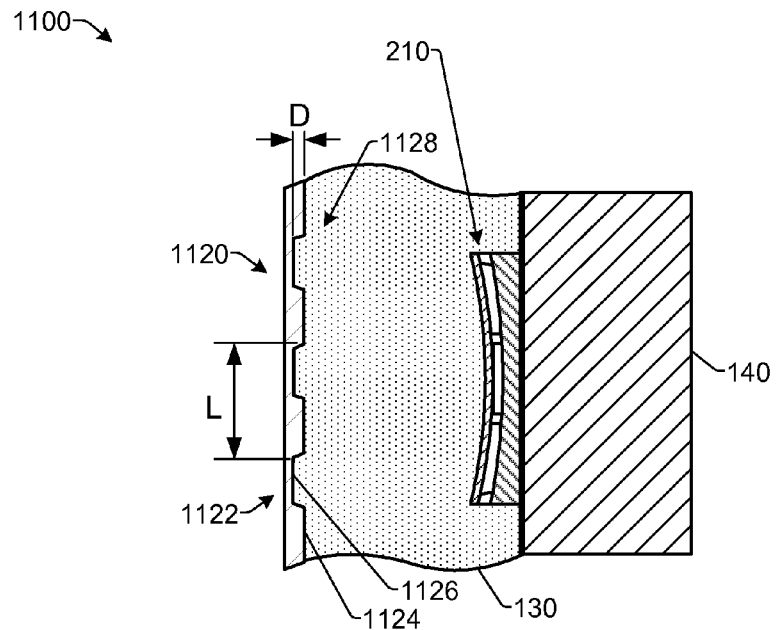
FIG. 11 illustrates a cross-sectional view of an example of a CMUT apparatus with an acoustic window having a planar shape with a multiple-step non-uniform thickness profile according to some implementations.

FIG. 11 illustrates a cross-sectional view of an example CMUT apparatus 1100 with an acoustic window 1120 according to some implementations. The CMUT apparatus 1100 may include a CMUT (or a CMUT array), such as the CMUTs 110 or 210 discussed above. In the illustrated example, the CMUT apparatus 1100 includes the CMUT 210, the acoustic window 1120, coupling medium 130, and CMUT packaging substrate 140. The thickness profile pattern of the acoustic window 1120 may be designed as a thickness profile having multiple steps. FIG. 11 shows an example acoustic window 1120 having a pattern 1122 that that includes two relatively defined thicknesses, i.e., a first thickness 1124 and a second thickness 1126, alternating at regular intervals. Thus, the pattern 1122 may be a surface pattern formed into at least one surface of the acoustic window 1120.

The geometric size of the thickness profile pattern 1122 may be in a range of 0.1 times to 10 times of the acoustic wavelength generated by the CMUT 210. For example, the range of a height D of the pattern 1122 may be in a range of 0.1 times to 1 times of the acoustic wavelength generated by the CMUT 210; and the range of a length L of the pattern 1122 may be designed in a range of 0.25 times to 10 times of the acoustic wavelength generated by the CMUT 210. In addition, the pattern 1122 of the acoustic window 1120 may be implemented as a plurality of periodic surface patterns 1122 as shown in FIG. 11. In some cases, the pattern 1122 may extend in one direction providing a plurality of elongated portions of different heights D. In other examples, the pattern 1122 may extend in two directions providing a checkerboard type arrangement of portions of different heights D. The pattern 1122 may alternatively be a non-periodic pattern having differing heights D and lengths L. In addition, an uneven surface 1128 of the pattern 1122 of the acoustic window 1120 illustrated in FIG. 11 faces the coupling medium 130 and the CMUT 210. In other examples, the uneven surface 1128 of the pattern 1122 may face the outside target medium (e.g. human tissue, etc.).

Figure 12:
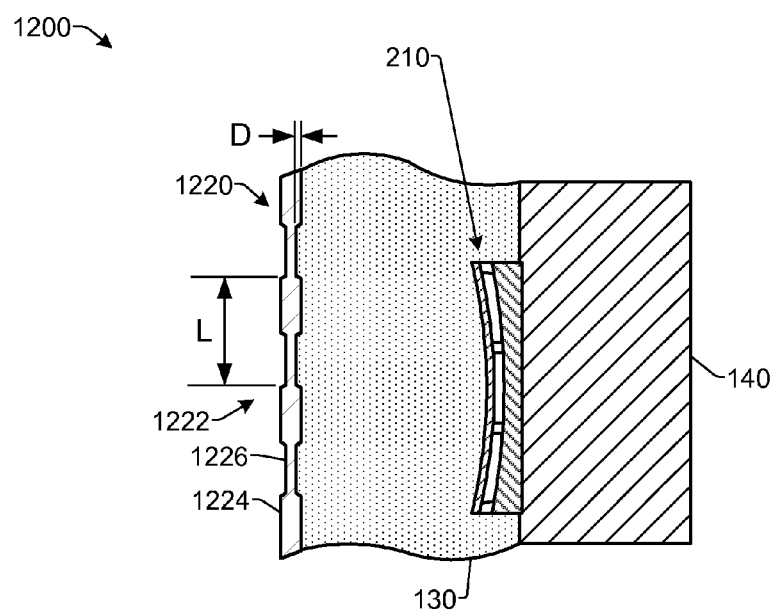
FIG. 12 illustrates a cross-sectional view of an example of a CMUT apparatus with an acoustic window having a planar shape with a multiple-step non-uniform thickness profile on multiple sides according to some implementations.

FIG. 12 illustrates a cross-sectional view of an example CMUT apparatus 1200 with an acoustic window 1220 according to some implementations. The CMUT apparatus 1200 may include a CMUT (or a CMUT array), such as the CMUTs 110 or 210 discussed above. In the illustrated example, the CMUT apparatus 1200 includes the CMUT 210, the acoustic window 1220, the coupling medium 130, and the CMUT packaging substrate 140. The thickness profile pattern 1222 of the acoustic window 1220 may be designed as a thickness profile with multiple steps. In this example, uneven surface patterns 1222 may be formed on both sides or surfaces of the acoustic window 1220, as shown in FIG. 12. Two uneven patterns 1222 may be aligned to provide a first thickness 1224 that alternates with a second thickness 1226 in a manner similar to that discussed above with respect to FIG. 11.

The geometric size of the thickness profile pattern 1222 may be designed in a range of 0.1 times to 10 times of the acoustic wavelength generated by the CMUT 210. For example, the range of a height D of the pattern 1222 may be in a range of 0.1 times to 1 times of the acoustic wavelength generated by the CMUT 210; and the range of a length L of the pattern 1222 may be designed in a range of 0.25 times to 10 times of the acoustic wavelength generated by the CMUT 210. In addition, the pattern 1222 of the acoustic window 1220 may be implemented as a plurality of periodic patterns 1222 as shown in FIG. 12. In some cases, the pattern 1222 may extend in one direction providing a plurality of elongated portions of different heights D on two sides of the acoustic window 1220. In other examples, the pattern 1222 may extend in two directions providing a checkerboard type arrangement of portions of different heights D on two sides of the acoustic window 1220. The pattern 1222 may alternatively be a non-periodic pattern having differing heights D and lengths L.

Figure 13:
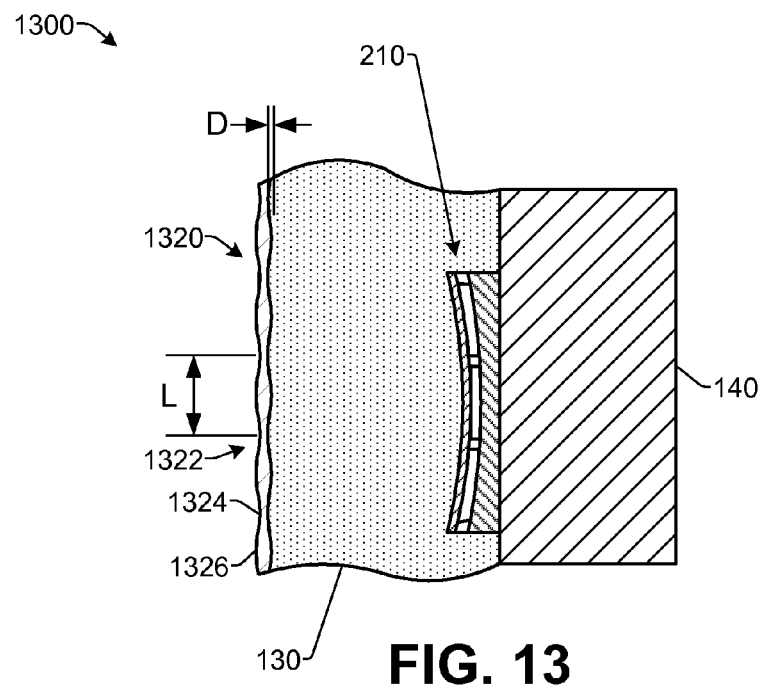
FIG. 13 illustrates a cross-sectional view of an example of a CMUT apparatus with an acoustic window having a planar shape with a gradually varied non-uniform thickness profile according to some implementations.

FIG. 13 illustrates a cross-sectional view of an example CMUT apparatus 1300 with an acoustic window 1320 according to some implementations. The CMUT apparatus 1300 may include a CMUT (or a CMUT array), such as the CMUTs 110 or 210 discussed above. In the illustrated example, the CMUT apparatus 1300 includes the CMUT 210, the acoustic window 1320, the coupling medium 130, and the CMUT packaging substrate 140. In the example, of FIG. 13, instead of the multiple-step profiles shown in FIGS. 11-12, the thickness profile of the acoustic window 1320 may gradually change, as illustrated in FIG. 13 in a pattern 1322 having a thin portion 1324 and a thick portion 1326. The geometric size of the thickness profile pattern 1322, shown in FIG. 13, may be in a range of 0.1 times to 10 times of the acoustic wavelength of the acoustic wave generated by the CMUT 210. For example, the range of a height D of pattern 1322 may be designed in a range of 0.1 times to 1 times of the acoustic wavelength generated by the CMUT 210; and the range of a length L of the pattern 1322 may be designed in a range of 0.25 times to 10 times of the acoustic wavelength generated by the CMUT 210. In addition, the pattern 1322 may be formed on both sides of the acoustic window 1320 or only on one side, and the pattern 1322 may be formed in one direction, or in two directions. Alternatively, the pattern 1322 may be also designed as a non-periodic pattern with different heights D and lengths L.

In FIGS. 11-13, the acoustic windows 1120, 1220, 1320 having non-uniform thickness profiles are illustrated using an example implementation with a flat acoustic window (e.g., related to the flat shape of the acoustic window 520 shown in FIG. 5). In other examples, the acoustic windows 1120, 1220, 1320 having a non-uniform thickness profile shown in FIGS. 11-13 may be also implemented for the acoustic windows with different shapes or positions. For example, the acoustic windows 1120, 1220, and 1320 may be provided with the tilted configuration of FIG. 8 and/or the convex or concave shapes of the acoustic windows shown in FIGS. 6-7.

As an alternative to the examples shown in FIGS. 11-13, any other type of surface roughness, pattern of indentations, or other surface pattern may be generated on the surface of the acoustic windows for use with the CMUT apparatuses herein. The geometric size of the pattern may be in a range of 0.1 times to 10 times of the acoustic wavelength of the acoustic wave generated by the CMUT 110, 210. For example, the range of a height of the pattern may be designed in a range of 0.1 times to 1 times of the acoustic wavelength generated by the CMUT 110, 210; and the range of a lateral size of the pattern indentations, etc., may be designed in a range of 0.25 times to 10 times of the acoustic wavelength generated by the CMUT 110, 210.

Figure 14:
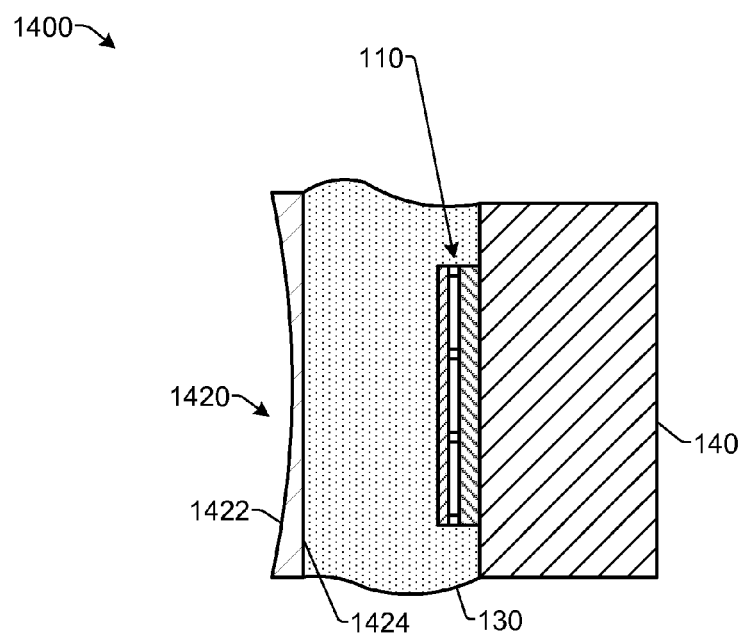
FIG. 14 illustrates a cross-sectional view of an example of a CMUT apparatus with an acoustic window that forms a concave lens with a flat surface adjacent to the coupling medium according to some implementations.

FIG. 14 illustrates a cross-sectional view of an example CMUT apparatus 1400 with an acoustic window 1420 according to some implementations. The CMUT apparatus 1400 may include a CMUT (or a CMUT array), such as the CMUTs 110 or 210 discussed above. In the illustrated example, the CMUT apparatus 1400 includes the CMUT 110, the acoustic window 1420, the coupling medium 130, and the CMUT packaging substrate 140. FIG. 14 illustrates an example implementation of a CMUT apparatus 1400 with the acoustic window 1420 having a focusing capability. The thickness profile of the acoustic window 1420 forms a concave lens. In this case, an outer surface 1422 of the acoustic window 1420 include a concave curvature to while an inner surface 1424 of the acoustic window 1420 adjacent to the coupling medium 130 may be flat so that the coupling medium does not contribute to the focus capability. Thus, in this example, there are more selections available for the material of the coupling medium 130 since the acoustic velocity or impedance of the coupling medium 130 is not a factor. Further, in any of the examples of FIGS. 14-20, the CMUT 210 may be used instead of the CMUT 110 to provide further focusing capability.

Figure 15:
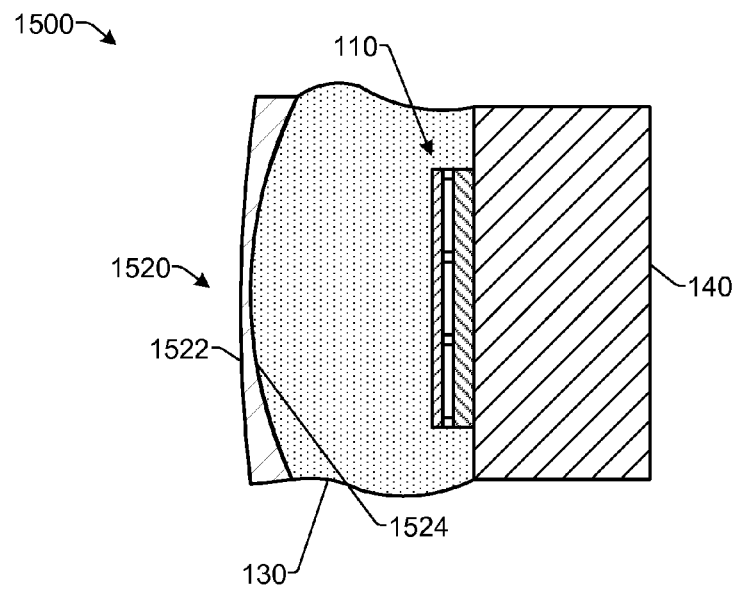
FIG. 15 illustrates a cross-sectional view of an example of a CMUT apparatus with an acoustic window forming a concave lens with a curved surface adjacent to the coupling medium according to some implementations.

FIG. 15 illustrates a cross-sectional view of an example CMUT apparatus 1500 with an acoustic window 1520 according to some implementations. The CMUT apparatus 1500 may include a CMUT (or a CMUT array), such as the CMUTs 110 or 210 discussed above. In the illustrated example, the CMUT apparatus 1500 includes the CMUT 110, the acoustic window 1520, the coupling medium 130, and the CMUT packaging substrate 140. In this example, the coupling medium 130 may also serve, at least in part, as an acoustic lens and may form a compound lens with the acoustic window 1520. The acoustic window 1520 may include an outer surface 1522 having a first curvature, and an inner surface 1524 of the acoustic window 1520 may have a second curvature, different from the first curvature. Depending on the velocity of the coupling medium 130, the second curvature of the inside surface of the acoustic window may be designed to be either more concave than the first curvature, as shown in FIG. 15. In such an arrangement, the coupling medium 130 may contribute to the focusing capability of the CMUT apparatus 1500. Additionally, in other examples, the second curvature may be less concave than the first curvature, or may alternatively be convex.

Figure 16:
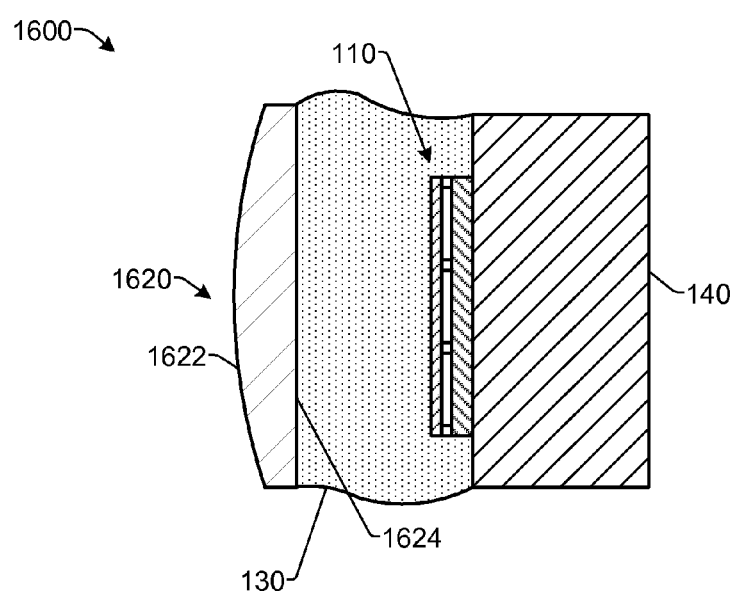
FIG. 16 illustrates a cross-sectional view of an example of a CMUT apparatus with an acoustic window forming a convex lens with a flat surface adjacent to the coupling medium according to some implementations.

FIG. 16 illustrates a cross-sectional elevation view of an example CMUT apparatus 1600 with an acoustic window 1620 according to some implementations. The CMUT apparatus 1600 may include a CMUT (or a CMUT array), such as the CMUTs 110 or 210 discussed above. In the illustrated example, the CMUT apparatus 1600 includes the CMUT 110, the acoustic window 1620, the coupling medium 130, and the CMUT packaging substrate 140. FIG. 16 shows another example implementation of a CMUT apparatus with the acoustic window 1620 having a focusing capability. The apparatus 1600 includes a thickness profile in which an outer surface 1622 of the acoustic window 1620 forms a convex lens. In this case, an inner surface 1624 of the acoustic window 1620 facing the coupling medium 130 may be flat so that the coupling medium 130 does not contribute to the focusing capability. In such an arrangement, there are more selections available for the material of the coupling medium 130 since the acoustic velocity or impedance of the coupling medium 130 is not a factor.

Figure 17:
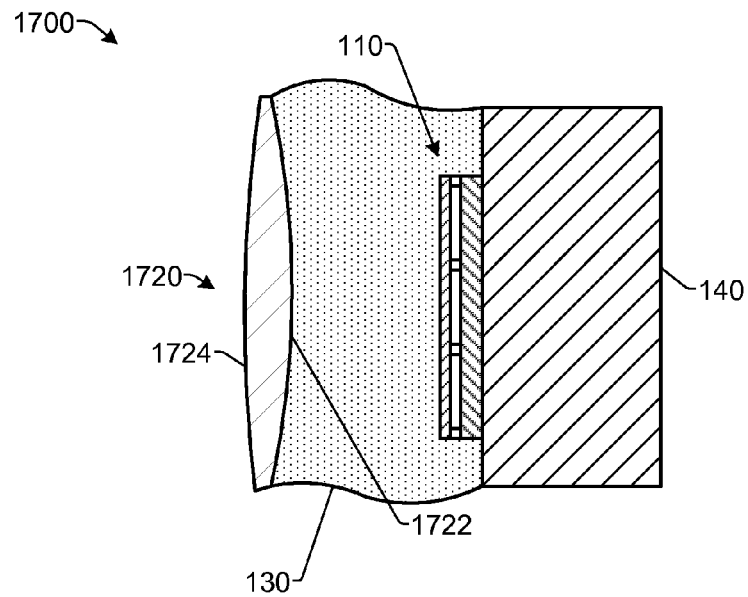
FIG. 17 illustrates a cross-sectional view of an example of a CMUT apparatus with an acoustic window forming a convex lens with a curved surface adjacent to the coupling medium according to some implementations.

FIG. 17 illustrates a cross-sectional elevation view of an example CMUT apparatus 1700 with an acoustic window 1720 according to some implementations. The CMUT apparatus 1700 may include a CMUT (or a CMUT array), such as the CMUTs 110 or 210 discussed above. In the illustrated example, the CMUT apparatus 1700 includes the CMUT 110, the acoustic window 1720, the coupling medium 130, and the CMUT packaging substrate 140. In this example, the coupling medium 130 may serve, at least in part, as an acoustic lens by forming a compound lens in conjunction with the acoustic window 1720. In this example, an inner surface 1722 of the acoustic window 1720 may have a desired curvature and an outer surface 1724 may be flat or may have a curvature also. Depending on the velocity of the coupling medium 130, the curvature of the inside surface 1722 of the acoustic window 1720 may be designed to be either convex as shown in FIG. 17 or concave, as discussed above with respect to FIG. 15.

In the example implementations shown in FIGS. 14-17, the uneven patterns (e.g., those patterns discussed above with respect to FIGS. 11-13) may be formed on either the inner or outer surface, or both surfaces, of the acoustic windows 1420-1720 to weaken the effects of acoustic reflection on the CMUT operation.

Figure 18:
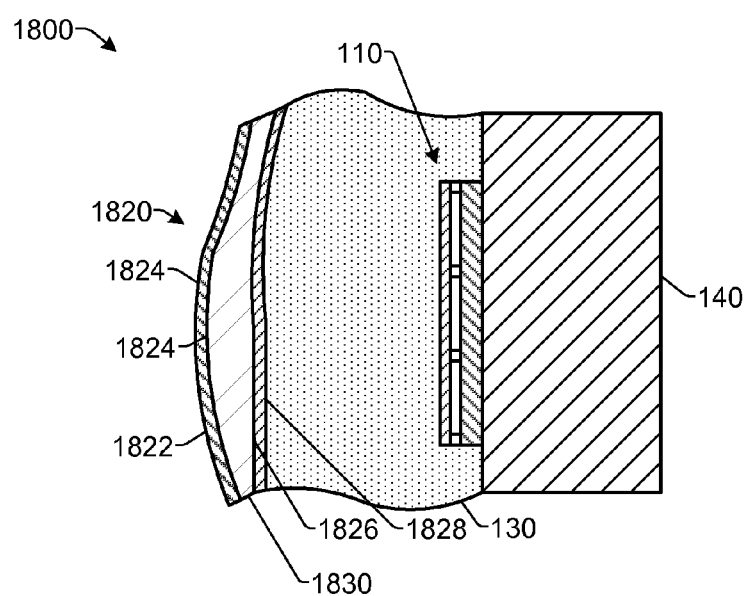
FIG. 18 illustrates a cross-sectional view of an example of a CMUT apparatus with an acoustic window made of multiple layers of materials according to some implementations.

FIG. 18 illustrates a cross-sectional elevation view of an example CMUT apparatus 1800 with an acoustic window 1820 according to some implementations. The CMUT apparatus 1800 may include a CMUT (or a CMUT array), such as the CMUTs 110 or 210 discussed above. In the illustrated example, the CMUT apparatus 1800 includes the CMUT 110, the acoustic window 1820, the coupling medium 130, and the CMUT packaging substrate 140. FIG. 18 illustrates an example in which the acoustic window 1820 may be made of multiple layers. For example, by selecting proper materials and layer thicknesses, the acoustic window 1820 may have desired acoustic and/or mechanical properties. For instance, by using multiple layers to build the acoustic window 1820, an anti-reflection coating layer 1822 may be formed on the acoustic window 1820. The coating layer 1822 may be deposited on either an outer surface 1824 or an inner surface 1826, or both surfaces 1824, 1826 of the acoustic window 1820.

In some examples, as illustrated, a different coating layer 1828 may be formed on the inner surface 1826, which is different from the coating layer 1822 formed on the outer surface 1824. As an example, if the acoustic impedance does not match between the acoustic window material 1830 and the target medium outside the CMUT apparatus 1800, a matching layer 1822 may be added. Further, if the acoustic impedance does not match between the acoustic window material 1830 and the coupling medium 130, a matching layer 1828 may be added. For example, the matching layers 1822, 1828 may have an acoustic impedance between the two unmatched mediums and the thickness of the matching layer may be ¼ or ½ of the acoustic wavelength generated by the CMUT 110 (or ¼ and ½ plus an additional full wavelength). The matching layers 1822, 1828 may be added on any implementation of the acoustic windows in this disclosure when the acoustic impedances do not match between the acoustic window and the other mediums. Thus, the acoustic window 1820 made of multiple layers of material may be used for any acoustic window, including, but not limited to, any of the implementations disclosed herein.

Figure 19A:
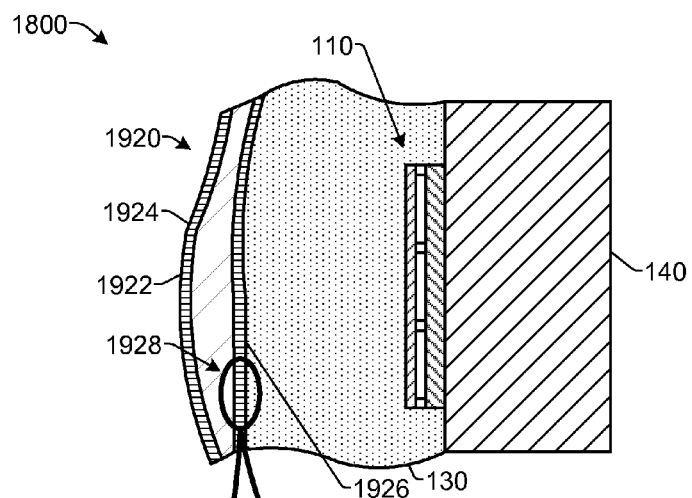
FIGS. 19A-19C illustrate an example of a CMUT apparatus with an acoustic window having multiple layers of materials according to some implementations.
Figure 19B:
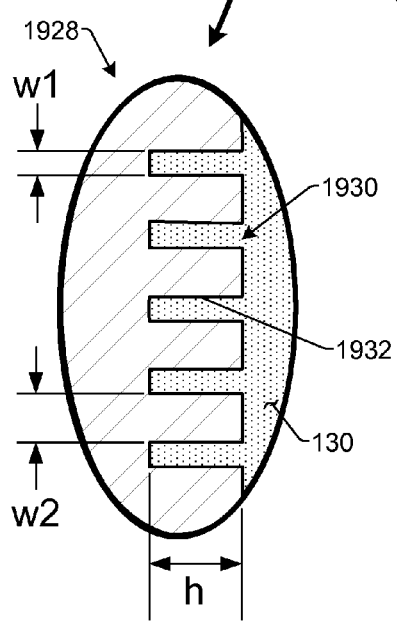
Figure 19C:
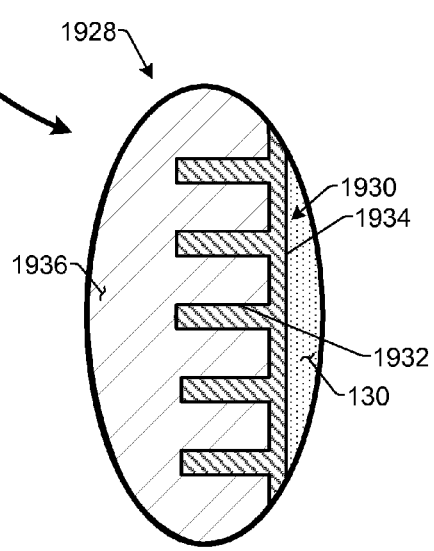

FIGS. 19A-C illustrate examples of a CMUT apparatus 1900 with an acoustic window 1920 according to some implementations. The CMUT apparatus 1900 may include a CMUT (or a CMUT array), such as the CMUTs 110 or 210 discussed above. In the illustrated example, the CMUT apparatus 1900 includes the CMUT 110, the acoustic window 1920, the coupling medium 130, and the CMUT packaging substrate 140. Moreover, instead of (or in addition to) coating a layer of selected material on the acoustic window as discussed above with respect to FIG. 18, in the example of FIG. 19A, at least a portion of the acoustic window 1920 may include a surface layer 1922 engineered to have desired material properties on at least one of an outer surface 1924 or an inner surface 1926.

FIG. 19B illustrates an enlarged view of an area of a surface layer 1928 at the inner surface 1926 from FIG. 19A, including an example structured surface layer 1930 of the acoustic window 1920 according to some implementations. The structured surface layer 1930 may include a plurality of trenches (or openings) 1932 formed into the surface layer 1930 of the material of the acoustic window 1920. The trenches (or openings) 1932 may have a height h, with a trench width w1 and a trench pitch w2, The trenches 1932 may be formed on either or both of the inner surface 1926 or the outer surface 1924 of the acoustic window 1920. In the example of FIG. 19B, the trenches 1932 may be filled with the material of the coupling medium 130 or an exterior medium, such as air or acoustic gel, in the case that the structured surface layer 1930 is formed on the outer surface 1922 of the acoustic window 1920. Thus, the structured surface layer 1930 has the acoustic properties different from both those of acoustic window material and the material filled into the trenches of the structured surface layer 1930. In some cases, the trenches 1932 may be formed in a single direction as a plurality of long parallel trenches. In other examples, the trenches 1932 may be formed in two directions, such as perpendicular to one another, to form a grid of trenches 1932.

Alternatively, as illustrated in FIG. 19C, the trenches 1932 may be filled with a filling material 1934. The acoustic properties of the surface layer 1930 may be defined by the acoustic properties of both the acoustic window material 1936 and the filling material 1934, as well as the geometry of the trenches (i.e., the height h, width w1, width w2 and patterns). Therefore, in some examples, the surface layer 1930 may be engineered to have desired acoustic properties. Either or both surfaces of the acoustic window 1920 may be engineered to have the surface layer 1930 with the desired properties. Thus, a suitable filling material 1934 having desired properties may be the same or similar to the coupling medium 130 and/or the external or target medium. Typically, according to the material used for the acoustic window, the filling material 1934 may be the same or similar to those example materials disclosed for the coupling medium and the acoustic window discussed above. In some examples, the filling material 1934 may have an acoustic impedance between the acoustic impedance of a window material 2034 and the acoustic impedance of the coupling medium 130 when used on the surface 1926 facing the coupling medium 130. The geometric size of the trenches 1932 may be designed in a range of 0.1 times to 10 times of the acoustic wavelength of the acoustic wave at which the CMUT 110 operates. For example, the range of the height h, the width w1 and the width w2 of the trenches 1932 may be designed to be less than 1.0 acoustic wavelength of the acoustic wave at which the CMUT operates. Particularly, the height h of the trenches 1932 may be designed to be ¼ or ½ of the acoustic wavelength generated by the CMUT 110 (or ¼ and ½ with an additional full wavelength).

FIGS. 20A-C illustrate an example CMUT apparatus 2000 with an acoustic window 2020 according to some implementations. The CMUT apparatus 2000 may include a CMUT (or a CMUT array), such as the CMUTs 110 or 210 discussed above. In the illustrated example, the CMUT apparatus 2000 includes the CMUT 110, the acoustic window 2020, the coupling medium 130, and the CMUT packaging substrate 140. Moreover, the acoustic properties of the acoustic window 2020 may be controlled according to a selected pattern for trenches formed into at least one of an outer surface 2022 or an inner surface 2024 of the acoustic window 2020.

For example, as illustrated in FIG. 20B, an enlarge portion 2026 of the acoustic window 2020 includes a structured pattern 2028 including a plurality of trenches (or openings) 2030. The acoustic properties of the acoustic window 2020 may be controlled based at least in part on how far the trenches 2030 extend, such as whether the trenches 2030 extend through a portion of the thickness of the acoustic window 2020 or entirely through. For example, the trenches may extend through any portion of the thickness of the acoustic window 2020 to a height h. Further, in some cases not all trenches will extend the same height h. In addition, the trenches may have a width w1 and a pitch w2, similar to the example described with respect to FIGS. 19A-C. In the example of FIG. 20, the trenches 2030 are filled with a filling material 2032. In some examples, the engineered transition layer on the acoustic window 2020 with the filling material 2032 may have an acoustic impedance between the acoustic impedance of a window material 2034 and acoustic impedance of the filling material 2032 or the coupling medium 130, such as when the trenches open to the side of the acoustic window facing the coupling medium.

Alternatively, as illustrated in FIG. 20C, the trenches (or openings) 2030 may extend entirely through the thickness of the acoustic window 2020. In some cases, the trenches may be holes, while in other cases, the trenches may be longitudinal channels formed in one or multiple directions, at least some of which are generally parallel to one another. The filling material 2032 may be filled into the trenches 2030. The properties of the filling material 2032 may be selected to achieve a desired overall acoustic performance, with the material of the acoustic window 2034 also being taken into consideration. The ranges of the width w1 of the window material 2034 and the width w2 of the trenches 2030 may be designed to be less than 1.0 of the acoustic wavelength at which the transducer operates. The structured surfaces and windows may be used for acoustic windows with any shape or thickness profile including any of those disclosed herein.

Figure 21:
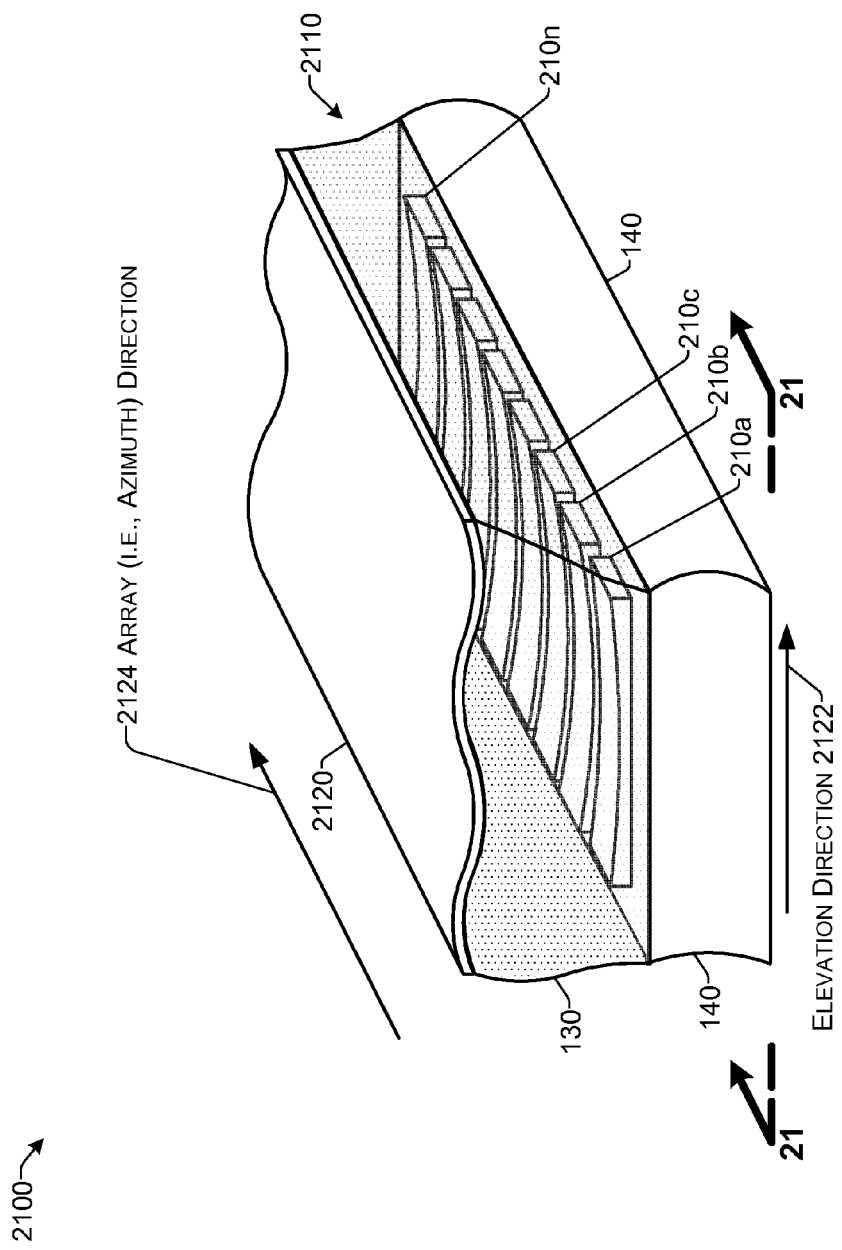
FIG. 21 illustrates a perspective view of an example implementation of a 1D CMUT array with an acoustic window according to some implementations.

FIG. 21 illustrates a perspective view of an example 1D CMUT array apparatus 2100 having an acoustic window 2120 according to some implementations. In the illustrated example, the acoustic window 2120 may correspond to the acoustic window 1020 described above with respect to FIG. 10, but any of the other acoustic windows, or combinations thereof, described herein may be used for the acoustic window 2120. For a 1D CMUT array, the acoustic effect of the acoustic window 2120 on each transducer element may be substantially the same. Accordingly, in examples that include a 1D array, FIGS. 1-20 may provide example cross section elevation views of the CMUT apparatuses along an elevation direction 2122 of 1D CMUT array as viewed along line 21-21 indicated in FIG. 21 (and rotated 90 degrees counterclockwise).

FIG. 21 shows an example perspective view of a 1D CMUT array apparatus 2100. The 1D CMUT apparatus includes a 1D CMUT array 2110, the acoustic window 2120, the coupling medium 130, and the CMUT packaging substrate 140. In this example, the 1D CMUT array 2110 includes multiple CMUTs 210a, 210b, 210c, . . . , 210n, each of which may be a fully functional CMUT transducer, as discussed above, such as with respect to FIG. 2. The acoustic window 2120 varies along the elevation direction 2122 of the 1D CMUT array 2110, and all the CMUTs 210 may have the same acoustic window effect along a transducer array direction 2124 (or azimuth direction) as indicated in FIG. 21.

Figure 22:
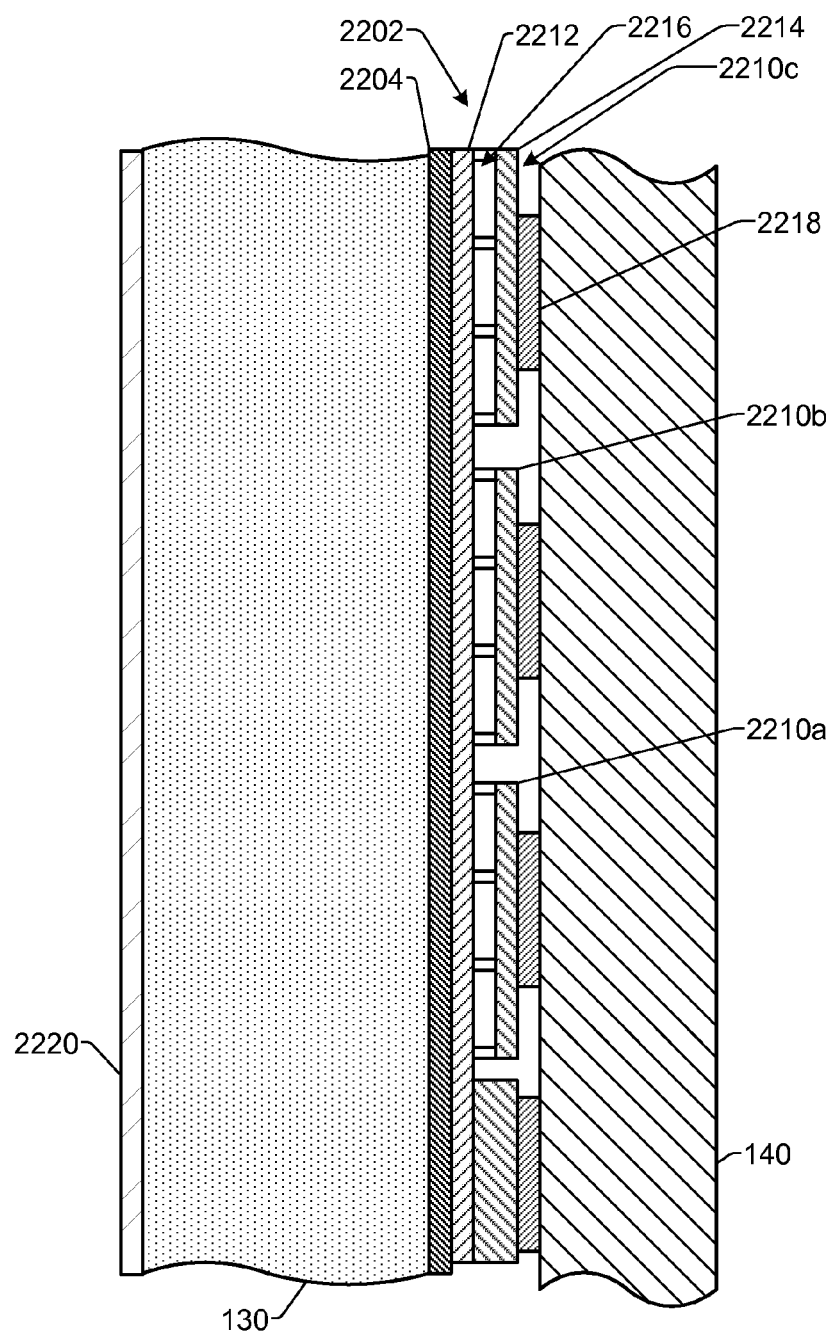
FIG. 22 illustrates a cross-sectional view of an example implementation of a CMUT array with an acoustic window according to some implementations.

FIG. 22 shows the cross-section view of an alternative CMUT array apparatus 2200 (e.g., for a 1D, 1.5D. 1.75D or 2D array, etc.) including an acoustic window 2220. The CMUT array apparatus 2200 includes a CMUT array 2202, the acoustic window 2220, the coupling medium 130, a CMUT protection layer 2204, and the CMUT packaging substrate 140. The CMUT array 2202 includes multiple CMUTs (e.g. 2210a, 2210b, 2210c, ...). Each CMUT 2210 may include at least a common first electrode 2212 and an individual second electrode 2214 separated by a transducing space 2216. For example, the common first electrode 2212 may be shared by multiple CMUTs 2210 in the CMUT array 2202. Moreover, the common electrode 2212 may be connected to an electrical ground (GND) (not shown in FIG. 22). The common electrode 2212 may be designed to face the coupling medium 130 and an individually addressed second electrode 2214 of each CMUT 2210 may be shielded by the common electrode 2212 from the coupling medium 130. On the packaging substrate 140, a pad 2218 may be provided between the second electrode 2214 and the packaging substrate 140 to connect to the second electrode 2214 of the CMUT 2210. As one example, one or more through-wafer interconnections may be fabricated to connect the electrodes 2212, 2214 of the CMUTs 2210 from the top surface of the CMUT fabrication substrate 2218 to a bottom surface.

In some examples, the protection layer 2204 may be coated onto the surface of the CMUTs 2210 to electrically isolate the CMUTs 2210 and the first electrode 2212 from the coupling medium 130. The protection layer 2204 may be any suitable insulating or dielectric material, such as poly(p-xylylene) (e.g., Parylene®), polyimide, oxide, nitride, RTV, urethane, polyurethane, non-conductive polymer, or other suitable plastic or rubber materials. The acoustic window 2220 may be any of the acoustic window configurations described herein.

Figure 23:
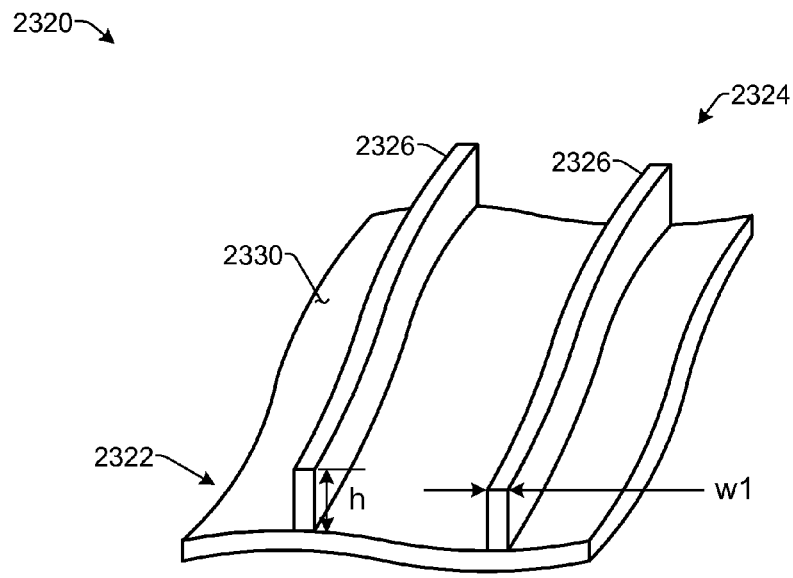
FIG. 23 illustrates an example of an acoustic window and a support structure according to some implementations.

FIG. 23 illustrates an example acoustic window 2320 having enhanced structural performance according to some implementations. For example, in order to improve the mechanical properties of the acoustic window 2320, one or more added structures may be introduced into the acoustic window 2320 to provide greater structural rigidity and strength with minimum impact on the acoustic performance of the CMUT apparatus. In the illustrated example, the acoustic window 2320 includes a base portion 2322 and one or more support structures 2324. The one or more support structures 2324 may be constructed from the same material as the base portion 2322 or from a material that is different from the material of the base portion 2322. The example acoustic window 2320 illustrated in FIG. 23 includes at least two elongated parallel beams 2326. The base portion 2322 may correspond to any of the examples of acoustic windows discussed above. In the illustrated example, the base portion 2322 includes an uneven surface, such as that described with respect to FIG. 10, and the beams 2326 may conform to the shape of the base portion 2322. Further, the beams 2326 may have a width w1, which may be uniform, or which may vary, and may have a height h, which may be uniform or which may vary.

In some examples, if a surface 2330 of the base portion 2322 having the beams 2326 located thereon faces the coupling medium 130 (not shown in FIG. 23), the spaces surrounding the beams 2326 may or may not be filled with a filling material. For example, in some cases, the coupling medium 130 may fill the space surrounding the beams 2326, while in other cases, a separate filling material may fill the space. Alternatively, if the surface 2330 and the beams 2326 of the acoustic window face outward from the transducer apparatus, then a suitable acoustic window material, as discussed above, may be selected to fill the space surrounding the beams 2326, as discussed below with respect to FIG. 25.

Figure 24:
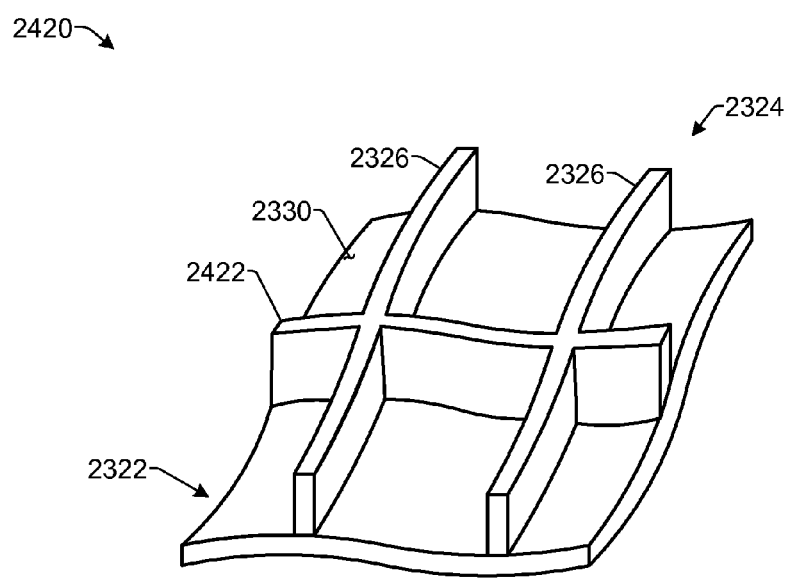
FIG. 24 illustrates an example of an acoustic window and a support structure according to some implementations.

FIG. 24 illustrates an example acoustic window 2420 having enhanced structural performance according to some implementations. In this example, the support structure 2324 includes the one or more beams 2326 discussed above, and one or more cross beams 2422. Further, as mentioned above, when the surface 2330 (with the beams 2326, 2422) of the acoustic window 2420 faces the coupling medium 130 (not shown in FIG. 24), the space around the beams 2326, 2422 may or may not be filled with suitable filling material. Alternatively, when the surface 2330 of the acoustic window 2420 faces outward from the CMUT apparatus, then a suitable filler material may be selected to fill the space around the beams 2326, 2422.

Figure 25:
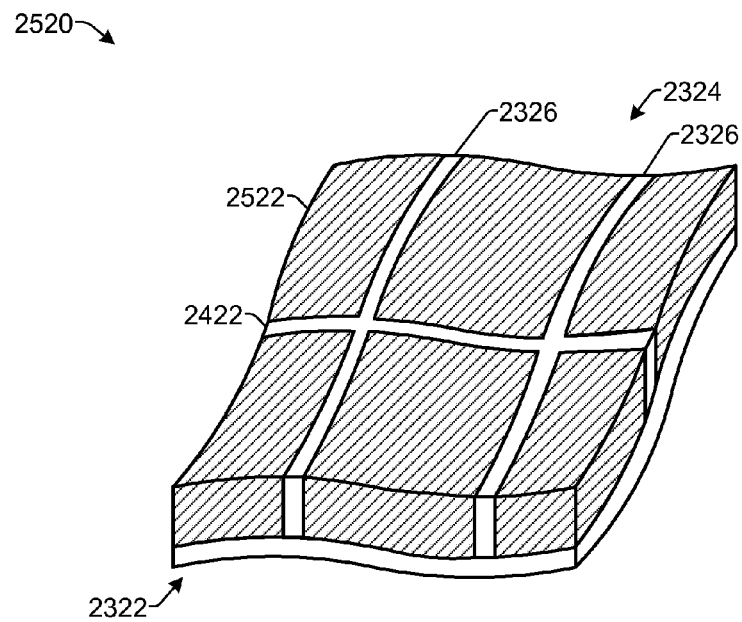
FIG. 25 illustrates an example of an acoustic window and a support structure according to some implementations.

FIG. 25 illustrates an example acoustic window 2520 having an enhanced structural performance according to some implementations. In this example, the acoustic window 2520 may include a basic structure, as discussed above with respect to FIG. 24, including one or more beams 2326 and one or more cross beams 2422. In this example, the space surrounding the beams 2326, 2422 is filled with a suitable filling material 2522. For example, the filling material 2522 may have an acoustic impedance that substantially matches the acoustic impedance of the material that the filling material 2522 contacts, i.e., either the coupling material 130 or the target medium 828, as well as matching the acoustic impedance of the material of the base 2322.

Figure 26:
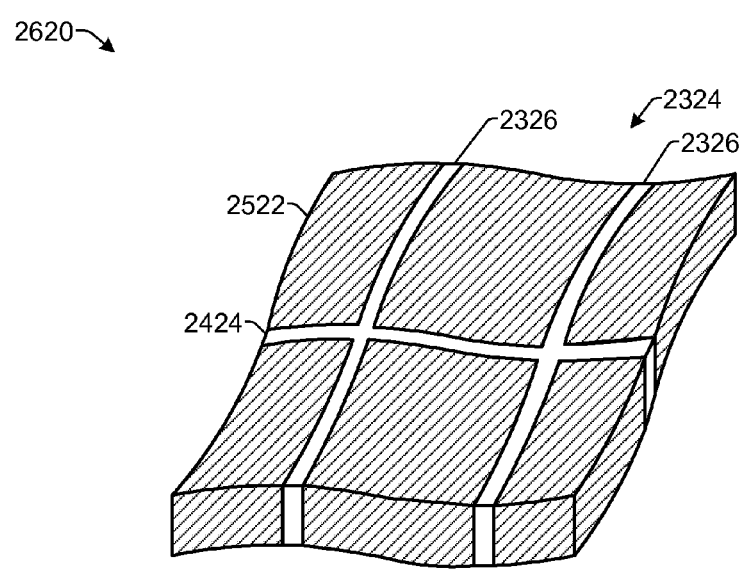
FIG. 26 illustrates an example of an acoustic window and a support structure according to some implementations.

FIG. 26 illustrates an example acoustic window 2620 having an enhanced structural performance according to some implementations. The acoustic window 2620 may include a portion of the structure described above with respect to FIGS. 24 and 25; however, in this example, if the filling material 2522 is sufficiently strong mechanically, the base portion 2322 may be eliminated from the acoustic window 2620, as shown in FIG. 26. In such a case, the acoustic window 2620 is made of the filling material 2522 with beams 2326 and or 2422, or other support structures 2324 embedded inside the filling material 2522. Typically, the support structures 2324 would be made of a material having a great mechanical strength or resistance to deformation than the filling material 2522, while the filling material 2522 may be selected based on acoustic impedance matching with mediums 130, 828 to be contacted. The support structures 2324 illustrated in FIGS. 23-26 are merely examples provided for discussion purposes. Other suitable shapes of support structures 2324 (i.e., hexagon or honeycomb, circles, etc.) may be used in other implementations, as will be apparent to those of skill in the art having the benefit of the disclosure herein.

The geometry of the support structure may be designed to maximize the mechanical strength and reliability of the acoustic window, while having minimum impact on the acoustic performance of the CMUT apparatus. To minimize the acoustic impact of the enhanced structure, the width w1 of the beams 2326, 2422 may be less than 1.0 acoustic wavelength at the frequency at which the CMUT operates. The height h of the beams 2326 may be selected to provide a desired amount of mechanical strength for the whole acoustic window. In some implementations, the materials of both the enhanced structure 2324 and the filling material 2522 may be selected from the materials discussed above as being suitable for the acoustic window and the coupling medium in some implementations. The acoustic windows with enhanced structures 2324 may be used for acoustic windows having any of the shapes or thickness profiles disclosed herein.

Example Process

Figure 27:
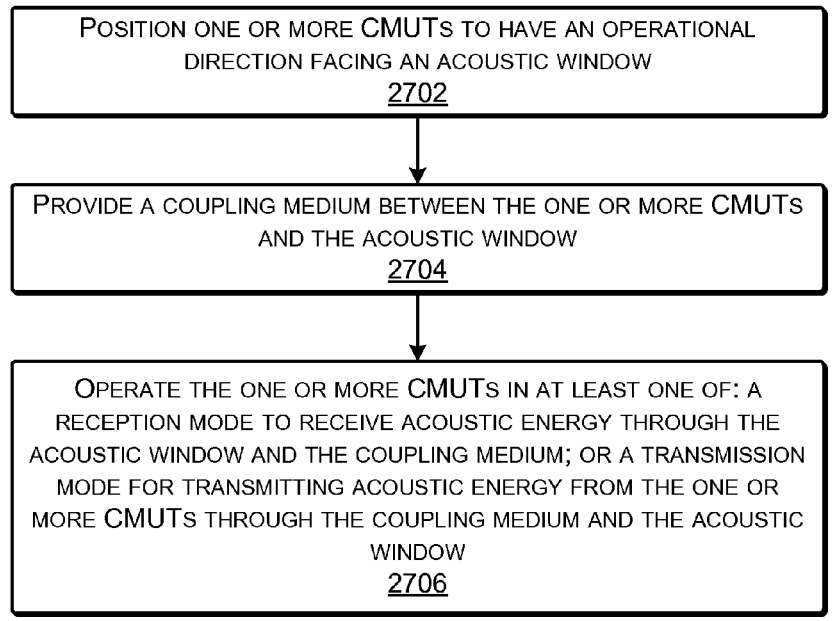
FIG. 27 is a flow diagram illustrating an example process for configuring and using a CMUT with an acoustic window according to some implementations.

FIG. 27 is a flow diagram illustrating an example process for a CMUT with an acoustic window according to some implementations.

At 2702, one or more CMUTs are positioned to have an operational direction facing an acoustic window. For example, the acoustic window may be constructed of a material suitable to contact a target medium. Thus, the acoustic window may have mechanical properties sufficient to withstand contacting the target medium and may have acoustic transmission properties similar to those of the target medium. Further, in some cases, the acoustic window may include a focusing capability, such as an acoustic lens for focusing acoustic energy on a focal location in the target medium. Alternatively, or additionally, the CMUT may include a focusing capability. Additionally, the acoustic window may include one or more features to reduce or minimize acoustic reflection, such as one or more patterns, coatings, structured layers, trenches, or the like, as described above. The acoustic window may further include one or more structural enhancements to improve the mechanical properties of the acoustic window.

At 2704, a coupling medium is provided between the one or more CMUTs and the acoustic window. For example, the coupling medium may be of a material having acoustic properties similar to those of the acoustic window and/or the target medium. The coupling medium may be enclosed or retained by a housing or the like. In some cases, the coupling medium may provide a focusing capability based, at least in part, on a configuration of the acoustic window.

At 2706, the one or more CMUTs are operated in at least one of: a reception mode to receive acoustic energy through the acoustic window and the coupling medium; or a transmission mode for transmitting acoustic energy from the one or more CMUTs through the coupling medium and the acoustic window. For example, the one or more CMUTs may be operated to transmit acoustic energy as an acoustic beam through the acoustic window when the acoustic window is placed into contact with a target medium. The acoustic window may include one or more features to minimize acoustic reflection of the acoustic beam. Further, in some examples, the acoustic window may be designed to focus the acoustic energy toward a focus location.

Additionally, the example process described herein is only one example of a process provided for discussion purposes. Numerous other variations will be apparent to those of skill in the art in light of the disclosure herein. Further, while the disclosure herein sets forth several examples of suitable apparatuses and environments for executing the process, implementations herein are not limited to the particular examples shown and discussed.

Furthermore, this disclosure provides various example implementations, as described and as illustrated in the drawings. However, this disclosure is not limited to the implementations described and illustrated herein, but may extend to other implementations, as would be known or as would become known to those skilled in the art. Reference in the specification to "one implementation," "this implementation," "these implementations" or "some implementations" means that a particular feature, structure, or characteristic described is included in at least one implementation, and the appearances of these phrases in various places in the specification are not necessarily all referring to the same implementation.

CONCLUSION

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

The invention claimed is:

1. A capacitive micromachined ultrasonic transducer (CMUT) apparatus comprising:
    one or more CMUTs;
    an acoustic window constructed of a first material; and
    a coupling medium constructed of a second, different material, the coupling medium to couple an acoustic wave between the one or more CMUTs and the acoustic window.

2. The CMUT apparatus as recited in claim 1, wherein the one or more CMUTs include a plurality of the CMUTs configured in one or more CMUT arrays, each CMUT array including multiple CMUTs.

3. The CMUT apparatus as recited in claim 1, wherein the one or more CMUTs include a focusing capability to, at least in part, direct the acoustic wave at a focal location.

4. The CMUT apparatus as recited in claim 3, wherein the focusing capability is due at least in part to a curvature of the CMUT active surface.

5. The CMUT apparatus as recited in claim 3, wherein the focusing capability is provided, at least in part, by the one or more CMUTs providing acoustic output having at least one of:
    a non-uniform phase distribution; or
    a non-uniform amplitude distribution.

6. The CMUT apparatus as recited in claim 1, wherein the acoustic window has a uniform thickness profile.

7. The CMUT apparatus as recited in claim 1, wherein the acoustic window has a non-uniform thickness profile.

8. The CMUT apparatus as recited in claim 1, wherein the coupling medium is liquid-based during operation of the CMUT apparatus.

9. The CMUT apparatus as recited in claim 1, wherein the coupling medium is solid-based.

10. The CMUT apparatus as recited in claim 9, wherein the coupling medium has a Young's modulus smaller than 5 Gpa.

11. The CMUT apparatus as recited in claim 1, wherein the coupling medium has a thickness that is larger than ¼ of a wavelength of an acoustic wave in a frequency at which the one or more CMUTs operate.

12. The CMUT apparatus as recited in claim 1, further comprising a housing attached to the acoustic window, wherein the housing maintains the coupling medium between the acoustic window and the one or more CMUTs.

13. The CMUT apparatus as recited in claim 1, wherein the acoustic window includes at least one curved surface.

14. The CMUT apparatus as recited in claim 13, wherein the curved surface is concave or convex with respect to an operational direction of the one or more CMUTs.

15. The CMUT apparatus as recited in claim 1, wherein a major plane of the acoustic window is positioned at an oblique angle with respect to an operational direction of the one or more CMUTs.

16. The CMUT apparatus as recited in claim 1, wherein the acoustic window includes a plurality of surface portions positioned at different angles with respect to an operational direction of the one or more CMUTs.

17. The CMUT apparatus as recited in claim 1, wherein the acoustic window includes at least one surface with a plurality of undulations.

18. The CMUT apparatus as recited in claim 1, wherein the acoustic window includes a pattern of variations in a thickness of the acoustic window.

19. The CMUT apparatus as recited in claim 1, wherein the acoustic window includes a coating on at least one surface to minimize acoustic reflection.

20. The CMUT apparatus as recited in claim 1, wherein the acoustic window includes a transition region on at least one of an inner surface facing the coupling medium or an outer surface to face a target medium.

21. The CMUT apparatus as recited in claim 20, wherein the transition region includes a plurality of trenches for receiving at least one of:
the coupling medium; or
a filling material.

22. The CMUT apparatus as recited in claim 20, wherein the transition region has an acoustic property that is between an acoustic property of the acoustic window and an acoustic property of at least one of:
the coupling medium; or
a target medium external to the CMUT apparatus.

23. The CMUT apparatus as recited in claim 20, wherein the transition region extends wholly or partially through the acoustic window.

24. The CMUT apparatus as recited in claim 1, wherein the acoustic window includes one or more structural support members.

25. The CMUT apparatus as recited in claim 24, further comprising an acoustic window fill material on at least one side of the one or more structural support members.

26. The CMUT apparatus as recited in claim 1, wherein an acoustic property of the acoustic window at the frequency range of operation of the one or more CMUTs is within an order of magnitude of an acoustic property of at least one of:
the coupling medium; or
a target medium external to the CMUT apparatus.

27. The CMUT apparatus as recited in claim 1, wherein the first material comprises at least one of:
polyethylene;
polyurethane;
polymethylpentene;
acrylonitrile butadiene styrene (ABS);
polycarbonate ABS;
thermoplastic polycarbonate;
polysulfone;
cross-linked polystyrene microwave plastic; or
a polyamide.

28. The CMUT apparatus as recited in claim 1, wherein the acoustic window includes a surface facing the coupling medium, the surface having a curvature such that the coupling medium focuses, at least in part, the acoustic wave.

29. A capacitive micromachined ultrasonic transducer (CMUT) apparatus comprising:
a CMUT substrate;
one or more CMUTs formed on the CMUT substrate, the CMUT substrate causing the one or more CMUTs to receive or emit acoustic energy in an operational direction;
an acoustic window to contact an external medium, the acoustic window positioned to pass the acoustic energy to or from the one or more CMUTs in the operational direction; and
a coupling medium to couple the acoustic energy between the one or more CMUTs and the acoustic window.

30. The CMUT apparatus as recited in claim 29, wherein:
the one or more CMUTs include a plurality of the CMUTs arranged in an array; and
at least some of the CMUTs in the array share a common electrode.

31. The CMUT apparatus as recited in claim 29, the acoustic window further including at least one structural feature to minimize reflection of the acoustic energy by the acoustic window.

32. The CMUT apparatus
as recited in claim 29, wherein the at least one structural feature includes at least one of:
an angled surface;
an undulated surface;
a patterned surface;
a coated surface;
a transition region; or
a variation in a thickness of the acoustic window.

33. The CMUT apparatus as recited in claim 29, wherein the one or more CMUTs include a focusing capability.

34. The CMUT apparatus as recited in claim 29, wherein the acoustic window includes a focusing capability.

35. A method comprising:
forming one or more capacitive micromachined ultrasonic transducers (CMUTs) on a CMUT substrate that positions the one or more CMUTs to have an operational direction facing an acoustic window, the acoustic window constructed of a material to contact a target medium;
providing a coupling medium between the one or more CMUTs and the acoustic window; and
operating the one or more CMUTs in at least one of:
a reception mode to receive acoustic energy through the acoustic window and the coupling medium; or
a transmission mode to transmit acoustic energy from the one or more CMUTs through the coupling medium and the acoustic window.

36. The method as recited in claim 35, wherein positioning the one or more CMUTs includes configuring at least one of the one or more CMUTs in a curved shape to focus acoustic energy at a focal location.

37. The method as recited in claim 35, further comprising providing a least one of an angled surface or a pattern on a least a portion of the acoustic window to minimize reflection of the acoustic energy by the acoustic window.

38. The CMUT apparatus as recited in claim 1, wherein the first material of the acoustic window includes a first acoustic property and the second material of the coupling medium includes a second, different acoustic property.

\* \* \* \* \*